US012157914B2

(12) United States Patent
Hall et al.

(10) Patent No.: US 12,157,914 B2
(45) Date of Patent: Dec. 3, 2024

(54) ELECTROCHEMICAL BIOSENSOR ARRAY DEVICES, SYSTEMS, AND METHODS FOR POINT-OF-CARE DETECTION

(71) Applicant: The Regents of the University of California, Oakland, CA (US)

(72) Inventors: Drew Hall, La Jolla, CA (US); Chung-Lun Hsu, Walnut, CA (US); Alexander Sun, San Mateo, CA (US); Yunting Zhao, San Diego, CA (US); Eliah Aronoff-Spencer, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1078 days.

(21) Appl. No.: 16/976,464

(22) PCT Filed: Feb. 28, 2019

(86) PCT No.: PCT/US2019/020137
§ 371 (c)(1),
(2) Date: Aug. 27, 2020

(87) PCT Pub. No.: WO2019/169192
PCT Pub. Date: Sep. 6, 2019

(65) Prior Publication Data
US 2021/0087614 A1 Mar. 25, 2021

Related U.S. Application Data

(60) Provisional application No. 62/636,784, filed on Feb. 28, 2018.

(51) Int. Cl.
*C12Q 1/6825* (2018.01)
*G01N 27/02* (2006.01)

(52) U.S. Cl.
CPC ......... *C12Q 1/6825* (2013.01); *G01N 27/028* (2013.01)

(58) Field of Classification Search
CPC .. C12Q 1/6825; G01N 27/028; A61B 5/1468; A61B 5/7203; A61B 5/7253; A61B 5/053
See application file for complete search history.

(56) References Cited

U.S. PATENT DOCUMENTS

2011/0268248 A1 11/2011 Kim et al.
2011/0282625 A1 11/2011 Craninckx et al.
(Continued)

OTHER PUBLICATIONS

Chen et al., Dual-mode urinalysis chip by using electrochemical impedance spectroscopy, 2011 Int. Conf. Intelligent Computation and Bio-Medical Instrumentation, 2011, DOI 10.1109/ICBMI.2011.55 (Year: 2011).*
(Continued)

*Primary Examiner* — Luan V Van
*Assistant Examiner* — Shizhi Qian
(74) *Attorney, Agent, or Firm* — Perkins Coie LLP

(57) ABSTRACT

Disclosed are biosensor devices, systems, and methods for point-of-care applications. In some aspects, a biosensor system includes a biosensor chip device to measure impedance at an electrode-electrolyte interface, which includes an electrochemical sensor comprising a first electrode including a functionalization layer exposing a molecular binding site to bind a target molecule for detection and a second electrode that does not include the binding site, and an electronic circuit unit corresponding to each electrode of the electrochemical sensor including a transimpedance amplifier, a phase detector to determine a relative phase shift in the detected electrical signal caused by an impedance change from a binding event of the target molecule at the molecular binding site, and a time-to-digital converter to quantize and average phase data points in time to remove uncorrelated
(Continued)

noise from the detected electrical signal; and a signal generator to produce an electrical excitation signal applied across the electrode-electrolyte interface.

24 Claims, 14 Drawing Sheets

Specification includes a Sequence Listing.

(56) References Cited

U.S. PATENT DOCUMENTS

| | | |
|---|---|---|
| 2013/0204103 A1 | 8/2013 | Maarek |
| 2014/0200336 A1 | 7/2014 | Kristensen et al. |
| 2014/0318958 A1* | 10/2014 | Hassibi .............. G01N 27/3277 204/403.01 |
| 2015/0068922 A1 | 3/2015 | Mackintosh |
| 2017/0172417 A1 | 6/2017 | Koomson et al. |

OTHER PUBLICATIONS

Manickam et al., A CMOS electrochemical impedance spectroscopy (EIS) biosensor array, IEEE Transactions on Biomedical Circuits and Systems, 2010, 4(6), 379-390 (Year: 2010).*
Huang et al., A TDC-based front-end for rapid impedance spectroscopy, 2013 IEEE 56th Int. Midwest Symp. on Circuits and Systems, p. 169-172 (Year: 2013).*
Sun et al., A multi-technique reconfigurable electrochemical biosensor: enabling personal health monitoring in mobile devices, IEEE transactions on biomedical circuits and systems, 2016, 10(5), 945-954 (Year: 2016).*
Straayer et al., A multi-path gated ring oscillator TDC with first-order noise shape, IEEE J. Solid-state circuits, 2009, 44(4) 1089-1098 (Year: 2009).*
Manickam et al., Interface design for CMOS-integrated electrochemical impedance spectroscopy (EIS) biosensors, Sensors, 2012, 12, 14467-14488 (Year: 2012).*
Ali et al. (Investigating phase detectors, 2015, 10.1109/MMM.2015.2478084 (Year: 2015).*
Daniels, An integrated impedance biosensor array, PhD thesis, Stanford University, 2010 (Year: 2010).*
Chen, T-A. et al. "Novel 10-Bit Impedance-to-Digital Converter for Electrochemical Impedance Spectroscopy Measurements" IEEE Transactions on Biomedical Circuits and Systems, vol. 11, No. 2, Apr. 2017, 370-379.
Huang, H. "Impedance Spectroscopy Front-end Suitable for Biomedical Cell Impedance Measurement" Thesis submitted Aug. 2013 to the Office of Graduate Studies of Texas A&M University. 83 pages.
ISA, International Search Report and Written Opinion for International Application No. PCT/US2019/020137. Mail Date: Jul. 11, 2019. 12 pages.
Manickam, A. et al. "A CMOS Electrochemical Impedance Spectroscopy Biosensor Array for Label-Free Biomolecular Detection" IEEE International Solid-State Circuits Conference, Feb. 2010, Session 6, Displays & Biomedical Devices. 3 pages.
Mazhab-Jafari, H. et al. "16-Channel CMOS Impedance Spectroscopy DNA Analyzer With Dual-Slope Multiplying ADCs" IEEE Transactions on Biomedical Circuits and Systems, vol. 6, No. 5, Oct. 2012, 468-478.
Yang, C. et al. "Compact Low-Power Impedance-to-Digital Converter for Sensor Array Microsystems" IEEE Journal of Solid-State Circuits, vol. 44, No. 10, Oct. 2009, 2844-2855.
Augustyniak Marcin, et al., "A 24x16 CMOS-Based Chronocoulometric DNA Microarray", ISSCC, 2006, pp. 59-68.
Elshazly, Amr, et al., "A Noise-Shaping Time-to-Digital Converter Using Switched-Ring Oscillators—Analysis, Design, and Measurement Techniques", IEEE Journal of Solid-State Circuits, vol. 49, No. 5, pp. 1184-1197.
Herne, Tonya M., et al., "Characterization of DNA Probes Immobilized on Gold Surfaces", J. Am. Chem. Soc. 1997, 119, pp. 8916-8920.

* cited by examiner

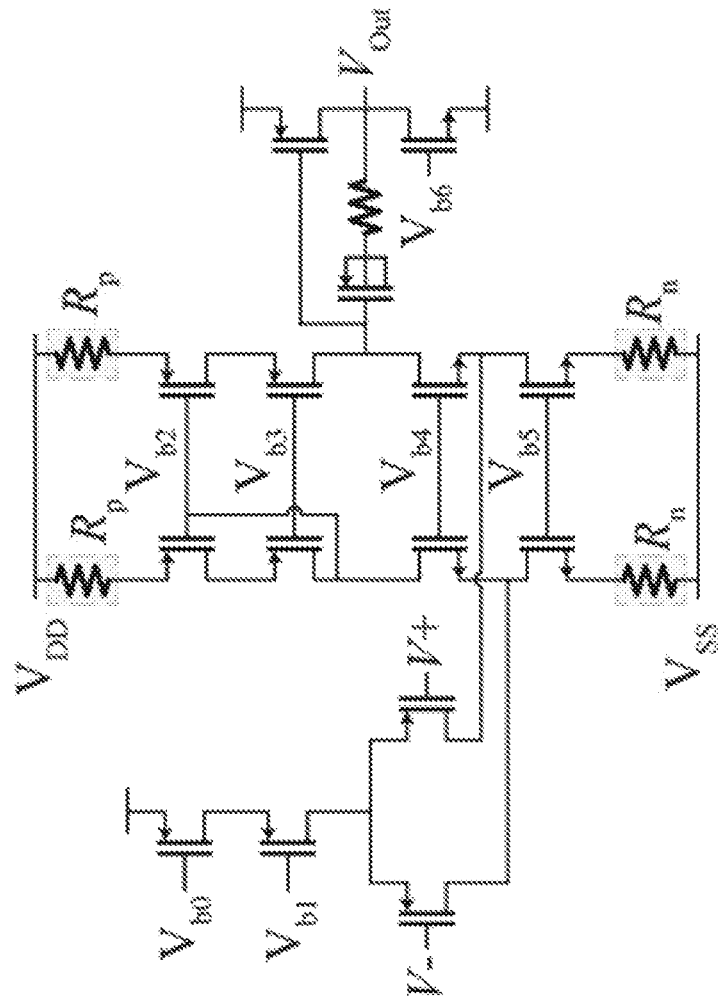
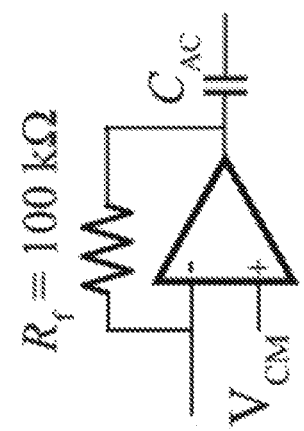
FIG. 4B
FIG. 4A

ELECTROCHEMICAL BIOSENSOR ARRAY DEVICES, SYSTEMS, AND METHODS FOR POINT-OF-CARE DETECTION

CROSS-REFERENCE TO RELATED APPLICATIONS

This patent document is a 371 National Phase Application of PCT Application No. PCT/US2019/020137 entitled "ELECTROCHEMICAL BIOSENSOR ARRAY DEVICES, SYSTEMS, AND METHODS FOR POINT-OF-CARE DETECTION", filed on Feb. 28, 2019, which claims priority to and benefits of U.S. Provisional Patent Application No. 62/636,784 entitled "ELECTROCHEMICAL BIOSENSOR ARRAY DEVICES, SYSTEMS, AND METHODS FOR POINT-OF-CARE DETECTION" filed on Feb. 28, 2018. The entire content of the aforementioned patent applications are incorporated by reference as part of the disclosure of this patent document.

REFERENCE TO SEQUENCE LISTING SUBMITTED VIA EFS-WEB

This application includes an electronically submitted sequence listing in .txt format. The .txt file contains a sequence listing entitled "009062-8374.US01_ST25.txt" created on Oct. 28, 2020 and is 803 bytes in size. The sequence listing contained in this .txt file is part of the specification and is hereby incorporated by reference herein in its entirety.

TECHNICAL FIELD

This patent document relates to biosensing devices, systems and methods.

BACKGROUND

Sensors based on electrochemical processes can be used to detect a chemical substance or a biological substance (e.g., an organism) by using a transducing element to convert a detection event into a signal for processing and/or display. Biosensors can use biological materials as the biologically sensitive component, e.g., such as biomolecules including enzymes, antibodies, nucleic acids, etc., as well as living cells. For example, molecular biosensors can be configured to use specific chemical properties or molecular recognition mechanisms to identify target agents. Biosensors can use the transducer element to transform a signal resulting from the detection of an analyte by the biologically sensitive component into a different signal that can be addressed by optical, electronic or other means. For example, the transduction mechanisms can include physicochemical, electrochemical, optical, piezoelectric, as well as other transduction means.

SUMMARY

Disclosed are devices, systems and methods for electrochemical biosensing for point-of-care applications. In some aspects, for example, the disclosed systems and devices include a field deployable biosensor array device for label-free nucleic acid detection having a unique architecture fabricated on a chip (e.g., CMOS chip) that enables in-pixel digitization and accumulation and increases the signal-to-noise ratio (SNR) of the biosensor array device, e.g., by 10 dB for each 10× increase in readout time. The example biosensor array devices and techniques are precise and highly scalable, e.g., enabling their use for point-of-care applications.

The example on-chip biosensors are operable for analyte detection using a streamlined and highly scalable phase detection method to monitor bioassay events, e.g., in which a polar mode biosensor records hybridization changes in the sensor capacitance, and in which the on-chip architecture provides in-pixel measurement by detecting the phase change between signal and reference electrodes. In some examples, an in-pixel circuitry (e.g., 140×140 $\mu m^2$) can measure the necessary phase changes of the on-chip sensors using a transimpedance amplifier, zero-crossing detector, and a first-order noise-shaping time-to-digital converter without the need for quadrature signal analysis.

In some aspects, a polar mode impedance biosensor system includes a biosensor chip device to measure impedance at an electrode-electrolyte interface, the biosensor chip including: an electrochemical sensor comprising a first electrode and a second electrode to detect an impedance change in a detected electrical signal at an outer surface of the electrode, and wherein the first electrode includes a functionalization layer on the outer surface of the electrode that includes one or more molecules exposing a molecular binding site to bind a target molecule for detection, and the second electrode does not include the one or more molecules attached to the outer surface, and an electronic circuit unit corresponding to each electrode of the electrochemical sensor, wherein each electronic circuit includes a transimpedance amplifier electrically coupled to the corresponding electrode to amplify the detected electrical signal, a phase detector in communication with the transimpedance amplifier to determine a relative phase shift in the detected electrical signal caused by the impedance change caused by a binding event of the target molecule with the molecular binding site of the one or more molecules, and a time-to-digital converter to quantize and average phase data points in time to remove uncorrelated noise from the detected electrical signal; and a signal generator to produce an electrical excitation signal applied (i) across the electrode-electrolyte interface to be measured by the transimpedance amplifier and (ii) at the phase detector in parallel in parallel.

In some aspects, a biosensor device includes a substrate comprising an electrically insulative material; a circuitry layer on the substrate, comprising a transimpedance amplifier, a phase detector, and a time-to-digital converter; and a sensing layer in electrical communication with the circuitry layer, comprising an array of sensor pixels including one or more reference sensor pixels and one or more signal sensor pixels arranged on the substrate, wherein the one or more signal sensor pixels include an electrode and a functionalization layer on the electrode including one or more molecules to provide a capture probe for a target analyte for detection, and the one or more reference sensor pixels include an unfunctionalized electrode spaced from a corresponding signal sensor pixel, wherein the biosensor device is operable to detect the target analyte based on electrical signal changes caused by hybridization of the capture probe by the target analyte.

In some aspects, a method for polar mode impedance biosensing includes applying an electrical excitation signal at a stimulation frequency across an electrode-electrolyte interface of an electrochemical sensor of a biosensor device; measuring an electrical signal at the electrochemical sensor using a transimpedance amplifier in communication with the biosensor device; determining a relative phase shift caused by a change of electrode impedance associated with caused by a molecular binding event of a target molecule with a molecular binding site of a functionalization layer of an electrode of the electrochemical sensor, and quantizing and averaging phase data points in time to remove uncorrelated noise from the detected electrical signal.

The subject matter described in this patent document can be implemented in specific ways that provide one or more of the following features.

BRIEF DESCRIPTION OF THE DRAWINGS

FIG. 4A shows a schematic of an example R-TIA with an AC-coupling capacitor.

FIG. 4B shows an example folded cascode amplifier with source degeneration to reduce flicker noise.

DETAILED DESCRIPTION

Point-of-care (POC) testing is essential to halt the spread of deadly infectious diseases, such as Ebola, Zika, and others, and is needed for rapid and accurate screening both in and outside of clinical settings. Label-free bioassays are desirable for POC testing as they have fewer reagents and assay steps resulting in lower cost and ease of use. Biosensors based on electrochemical impedance spectroscopy (EIS), an ultra-sensitive, label-free sensing technique, are a promising technology for precise and rapid disease diagnosis at the point-of-care. Generally, some EIS devices can provide label-free sensing with sensitivity and capability to scale fabrication of electrochemical sensors using standard semiconductor processes. However, conventional EIS techniques usually require expensive, complex and large-size electronic equipment and techniques, such as mixers and lock-in detection, to measure both the magnitude and phase of the complex impedance.

Electrochemical sensors, particularly EIS-based, for example, have been applied to many applications including antibody-antigen binding events and DNA hybridization. EIS sensors operate by measuring the impedance change at the interface between an electrode and an electrolytic solution that changes due to a binding event on the surface. Using conventional EIS sensor devices, EIS assays are typically constructed such that only a single component of the sensor's impedance is modulated by binding events, e.g., the change of the diffusion layer capacitor, $C_O$, as DNA hybridizes.

Figure 1A:
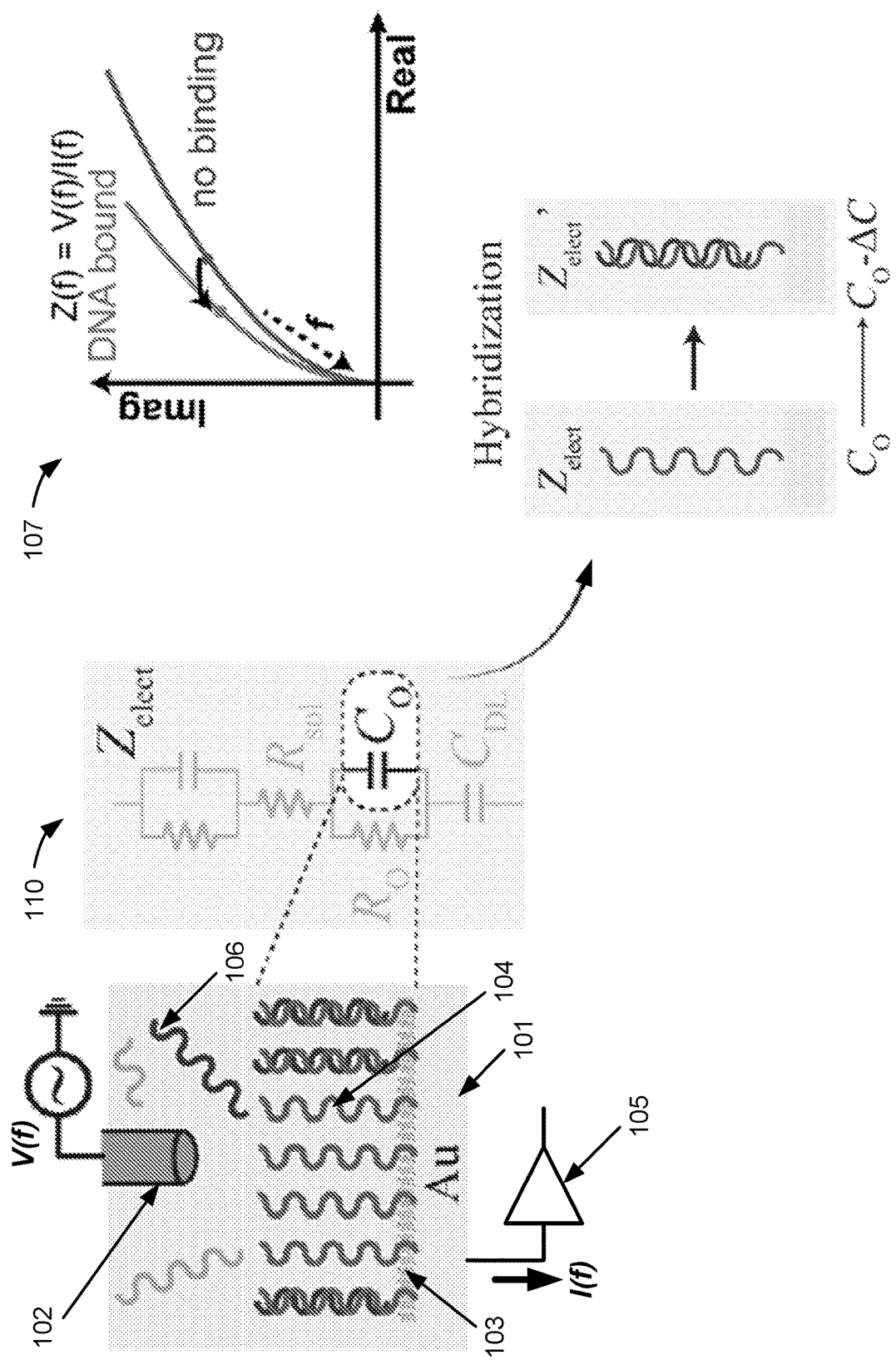
FIG. 1A shows a diagram illustrating the detection concept of electrochemical impedance spectroscopy (EIS) biosensing where a hybridization/binding event changes the sensor capacitance.

FIG. 1A shows a diagram illustrating the concept of EIS biosensing where a hybridization and/or binding event changes the sensor capacitance. As shown in the illustration on the left, a biosensor electrode, which includes an excitation (counter) electrode 102 and a detection (working) electrode 101, is interfaced to an amplifier 105 (e.g., transimpedance amplifier (TIA)) to detect a change in an electrical signal associated with a molecular binding (e.g., nucleic acid hybridization) of a target molecule 106 in an electrolytic solution and a complimentary molecule 104 (e.g., single-stranded nucleic acid with complimentary sequence to the target molecule 106) that is bound to the detecting electrode 101. In some examples, the complimentary molecule 104 is included in a monolayer 103 bound to the surface of the working electrode 101. As illustrated in the diagram, only a single component of the sensor's impedance is effectively modulated by binding events, e.g., the change of the diffusion layer capacitor, $C_O$, as the target molecule binds (e.g., hybridizes) with the complimentary molecule 104. This capacitance change, $\Delta C$, is indicative of the binding event at the surface of the working electrode 101, which shifts the monitored impedance, as shown by plot 107.

Figure 1B:
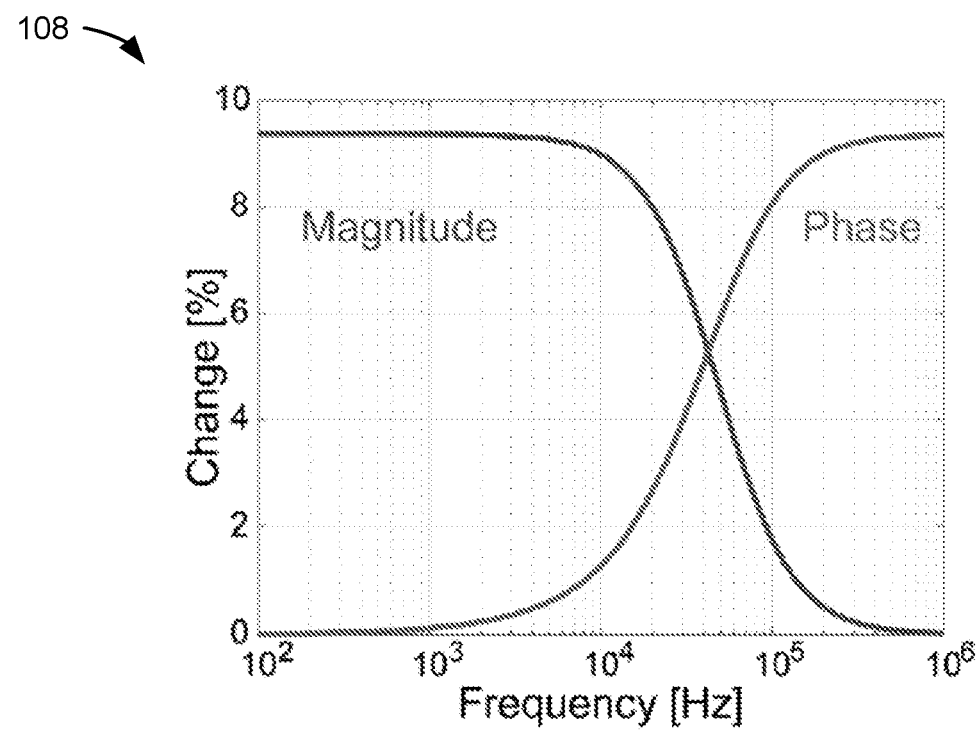
FIG. 1B shows data plots depicting magnitude and phase measurements for an example 100 nF capacitance change in an electrochemical cell.
Figure 1B:
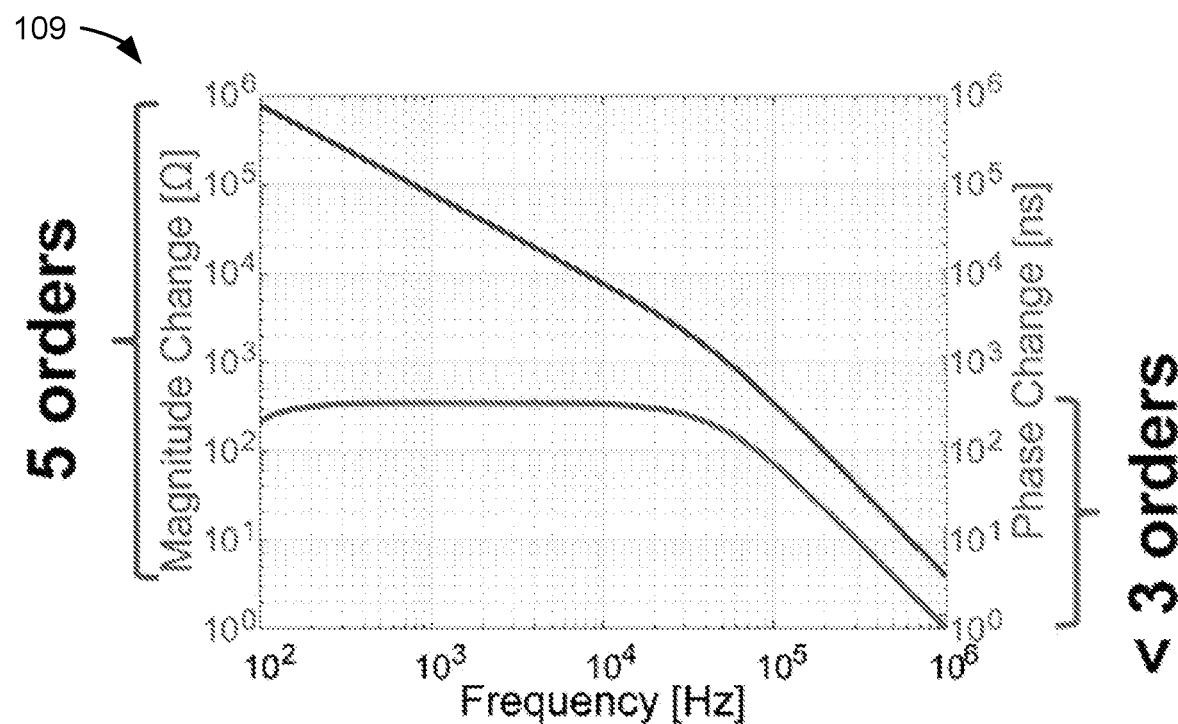

FIG. 1B shows data plots depicting magnitude and phase measurements for an example 100 nF capacitance change. As shown in plot 108, the capacitance change affects both magnitude and phase similarly; whereas in plot 109, the absolute magnitude is shown to span a larger range by the effect. As such, monitoring the phase within a relatively smaller frequency range than the magnitude can realize the same effects caused by capacitance changes.

Referring back to FIG. 1A, in the electrochemical measurement, the EIS device is exciting the electrochemical 'cell' with a stimulus waveform, e.g., V(f) voltage applied at the excitation electrode 102, and measuring the response at the working electrode 103 as an electrical signal, e.g., the resultant current I(f) flows at the working electrode 103 based on the stimulus waveform across the electrochemical cell, which can be modeled by the equivalent circuit model 110 (e.g., the Randles circuit). When the target molecule 106 in the electrolytic solution (e.g., DNA strand) binds to the complimentary molecule 104 (e.g., complimentary DNA strand) attached to the detection electrode 101, the impedance of the electrochemical cell is perturbed. The perturbation is an 'adjustment' to the resistive and capacitive part of the complex impedance of the electrochemical cell, illustrated by the plot 107.

Figure 1C:
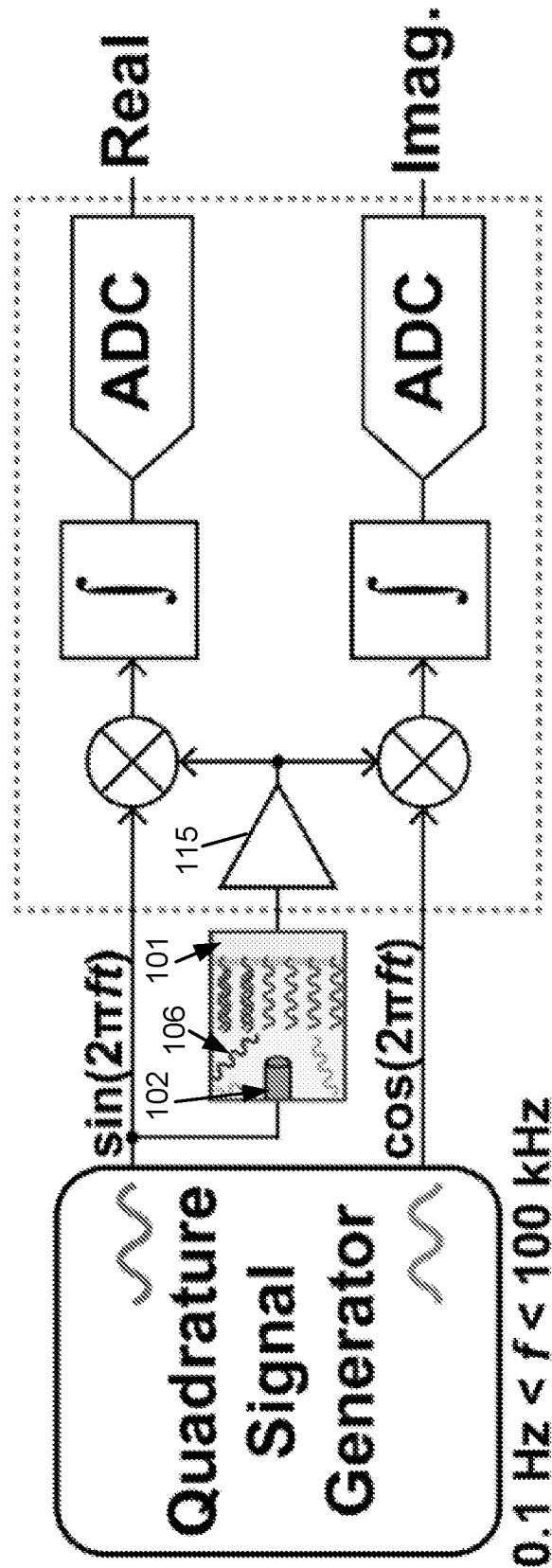
FIG. 1C shows a diagram of a conventional EIS technique to monitor changes in an electrochemical cell by a sensor caused by molecular binding events.

FIG. 1C shows a diagram of a conventional EIS technique to interrogate the electrochemical cell and perturbations caused by the binding events. Typically, such EIS measurements use a lock-in amplifier technique, where a sinusoidal signal (sin($2\pi ft$)) is applied at the excitation electrode 102 such that the response of the applied sinusoid is measured at the working electrode 101 by a transimpedance amplifier 115, which is mixed with the original sinusoidal signal (in-phase signal) and with a cosine of that signal (cos($2\pi ft$)) (quadrature-phase signal) to output a digitized real and imaginary part of the measured impedance.

Existing EIS sensor devices and systems typically measure the real and imaginary components of the complex impedance with a lock-in amplifier where the bandwidth is inversely proportional to the measurement time. Since the assay is often designed to modulate specifically the resistance or capacitance, traditional EIS approaches require additional hardware and computation to extract the information.

Disclosed are devices, systems and methods for polar mode electrochemical biosensing for point-of-care applications. In some aspects, example embodiments of field-deployable biosensor array devices for label-free molecular detection are disclosed, which have a specialized architecture to provide in-pixel digitization and accumulation of the detected signals with increased signal-to-noise ratio (SNR).

The disclosed polar mode biosensor devices, systems and methods are configured to measure and analyze the magnitude and phase of the impedance signal across the electrode-electrolyte interface in the electrochemical cell. In some implementations, example embodiments of the biosensor devices, systems and methods are configured to measure and analyze the only phase of the impedance signal. For example, the capacitance shift due to molecular interactions like antigen-antibody binding, DNA hybridization, etc. causes a significant and proportional change to the phase with only a minor variation in the amplitude. Thus, only part of the complex impedance, in this case the phase, is required for binding detection allowing the readout circuitry to be simplified. The sensor and circuit architecture of the disclosed biosensor array devices, systems and methods are designed to leverage this property for enabling individual hybridization and/or binding events of molecules on the detection region of a biosensor electrode.

Example Embodiments of the Polar Mode Biosensor Architecture

Figure 2A:
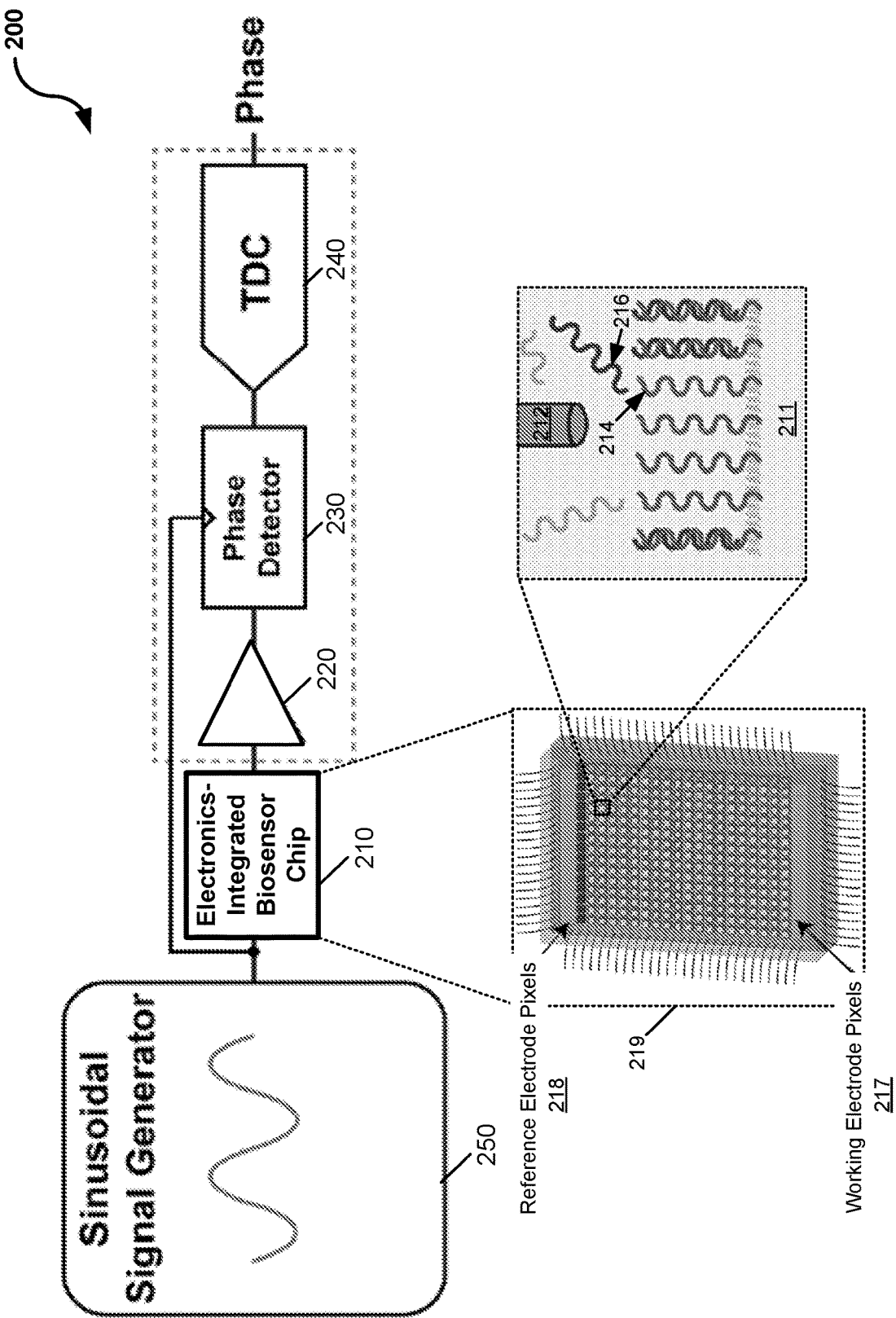
FIG. 2A shows a diagram depicting an example embodiment of an electrochemical impedance biosensor measurement system in accordance with the present technology configured for a phase-only detection and in-pixel analysis.

FIG. 2A shows a diagram depicting an example embodiment of an electrochemical impedance biosensor measurement system 200 in accordance with the present technology configured for a phase-only detection and in-pixel analysis, which includes an electronics-integrated biosensor chip 210, a signal amplifier 220 (e.g., transimpedance amplifier), a phase detector 230, a time-to-digital converter 240, and a signal generator 250. The example transimpedance amplifier 220 is electrically coupled to the electrodes of the biosensor chip 210 and in communication with the phase detector 230. The signal generator 250 provides a stimulus or excitation signal, e.g., a sinusoidal signal (sin($2\pi ft$)), through the electrochemical cell to be measured by the transimpedance amplifier 220 and directly to the phase detector 230, e.g., in parallel. The phase detector 230 is in communication with the time-to-digital converter 240 to measure the phase of the response signal ($\varphi_g$) detected at the working electrode 211 of the biosensor chip 211 for determining the phase change ($\varphi_{diff}$) caused by a binding event of the target molecule 216 with the complementary molecule 214 at the working electrode 211 with respect to the phase of the reference sensor ($\varphi_{ref}$).

For example, by implementing a phase-only detection of the impedance, the electrochemical impedance biosensor measurement system 200 enables the in-pixel averaging. For example, each instance where the excitation signal, e.g., a sinusoidal signal, is inputted to the electrochemical cell of the electronics-integrated biosensor chip 210, the system 200 measures the response, the response signal is delayed by a finite amount, indicative by the phase difference ($\varphi_{diff}$).

In some embodiments, for example like that shown in inset 219, the biosensor chip 210 can be configured as a high-density (e.g., 16×20 pixel) impedance biosensor array with on-chip sensors and in-pixel circuitry uses a polar mode impedance measurement scheme to improve both the scalability and sensitivity. For example, in some embodiments, the biosensor chip 210 is included on a single chip with an electronics unit that includes the in-pixel circuitry of the signal amplifier 220, the phase detector 230 and the TDC 240. Whereas, in some embodiments, the signal amplifier 220, the phase detector 230 and the TDC 240 can be included in an electronics unit that is external to the biosensor chip 210.

In some implementations, for example, the biosensor chip 210 can be embodied and can operate as follows. An external electrode (e.g., Ag/AgCl electrode) applies an excitation signal (e.g., 10 mV sinusoidal excitation) at a frequency, $f_{stim}$, e.g., between 1 mHz and 10 MHz, to the electrolytic solution. In some implementations, for example, the excitation signal is applied at $f_{stim}$ frequencies in a range between 10 mHz to 1 MHz. In this example, the biosensor chip includes an array of electrodes, in this example, a 100×100 $\mu m^2$ gold electrode array for the 16×19 working electrode pixels 217 and 16×1 reference electrode pixels 218, where the signal sensor electrodes are functionalized with molecules 214 capable of binding to the target molecule 216 (such as single-stranded nucleic acid molecules (e.g., single-stranded DNA)), and where the reference sensor electrodes are unfunctionalized or blocked. In some implementations, for example, the reference sensors are meant to account for global variations in the electrochemical cell and provide a phase reference that all of the sensors will be compared against. The corresponding induced current is measured with the example transimpedance amplifier 220, which can then be converted to a rail-to-rail signal by a zero-crossing detector, for example (as shown later in FIG. 2B). The remaining signal path consists of a phase detector 230 determining the relative phase shift caused by the change of electrode impedance. In some embodiments, the phase detector 230 includes an XOR logic gate; whereas in some embodiments the phase detector 230 can include a sample and hold circuit, a charge pump, or a logic gate including flip-flops. In some embodiments, the biosensor chip 210 can provide an analog signal to the phase detector 230, such that the phase detector 230 includes an analog phase detector, e.g., such as a mixer-based detector, after which the output can be digitized. The determined phase shift is quantized and averaged using the time-to-digital converter 240, e.g., with first-order noise-shaping.

Figure 2B:
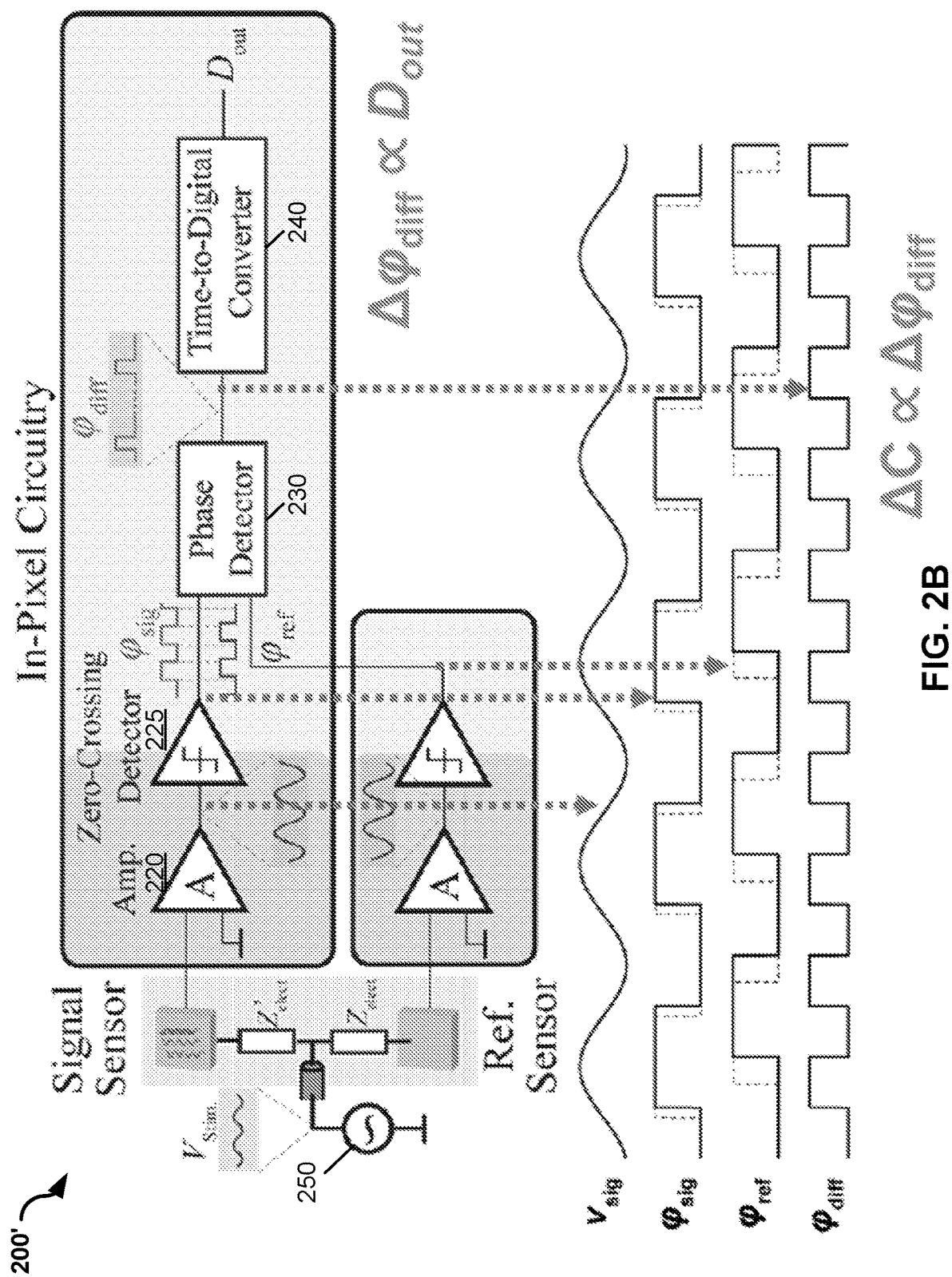
FIG. 2B shows an illustration of an example system architecture depicting an in-pixel measurement using an example embodiment of an on-chip biosensor device in accordance with the present technology by detecting the phase change between signal and reference electrodes.

FIG. 2B shows an illustration of an example embodiment of a system 200', in accordance with the example embodiments of the system 200, depicting an in-pixel measurement using an example on-chip biosensor device by detecting the phase change between signal and reference electrodes. As shown in the diagram, the signal generator 250 provides the excitation signal $V_{stim}$, e.g., a sinusoidal signal (sin(2πft)), through the electrochemical cell of the biosensor chip 210 such that the working electrode pixels 218 and the reference electrode pixels 219 of the array detect a change in the electrode impedance, shown as $Z'_{elect}$ and $Z_{elect}$ for the working electrode pixels ("sensor signal") and reference electrode pixels ("reference sensor"), respectively. The detected electrical signals (e.g., induced current) at these respective electrode pixels are measured at their respective in-pixel transimpedance amplifier 220, which can subsequently be further signal-processed, e.g., by an example zero-crossing detector 225, prior to phase detection of the signals by the phase detector 230. Using (i) the sensor signal phase ($\varphi_{sig}$) measured at the molecularly-modified working electrode and the reference signal phase ($\varphi_{ref}$) measured at the unmodified reference electrode pixels, which corresponds to the phase of the excitation signal, the phase detector 230 determines the relative phase shift caused by the change of electrode impedance, which is quantized and averaged by the TDC 240. The TDC 240 provides the in-pixel averaging to the measured sampled points in time based on the number of cycles to remove uncorrelated noise from the signal and improve the detection sensitivity and SNR.

The signal waveform plot in FIG. 2B (and further in greater detail for an example in FIG. 3) shows the reference signal ($\varphi_{ref}$), the response signal ($\varphi_{sig}$) and the difference between the reference and response signal phases ($\varphi_{diff}$). The plots show that, in implementations of the system 200 including the phase-only detection data path, the phase difference signal ($\varphi_{diff}$) is averaged to remove uncorrelated noise present in measured signals (e.g., white noise) and improve the SNR of the outputted impedance signal phase. The averaging technique averages out any uncorrelated noise with the root N number of measurements.

The disclosure below further describes example embodiments for the in-pixel circuitry architecture and example implementations of an example embodiment of the biosensor array device, including example measurement results.

Polar Phase Detection

Figure 2C:
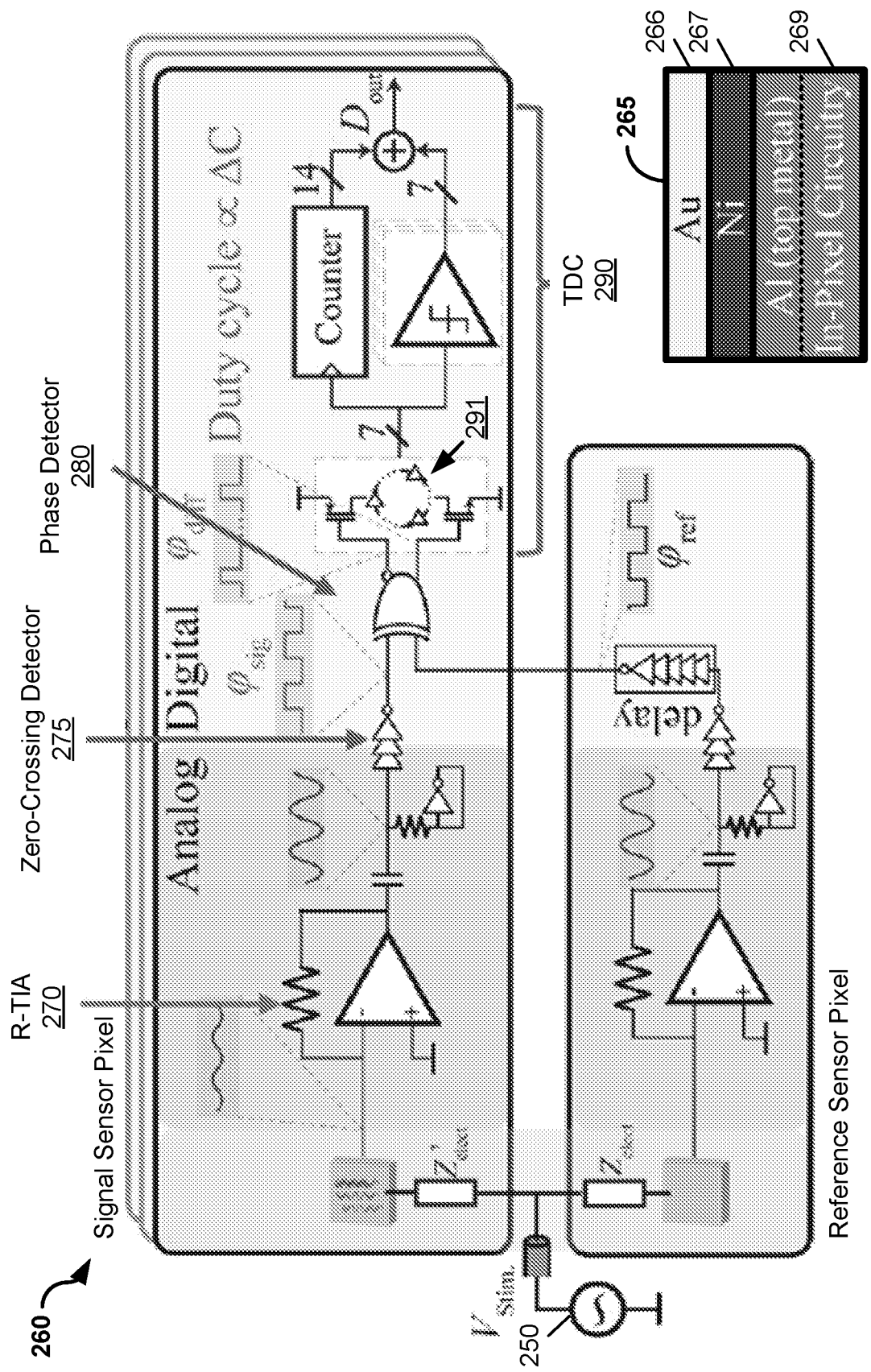
FIG. 2C shows a diagram depicting an example embodiment of the electrochemical impedance biosensor measurement system depicting an in-pixel measurement by a sensor pixel of an example on-chip biosensor device with in-pixel digitization.

FIG. 2C shows a diagram of another example embodiment of a system 260, in accordance with the example embodiments of the system 200 depicting an in-pixel measurement by a sensor pixel of an example on-chip biosensor device with in-pixel digitization. As shown in the diagram, for example, the induced currents are measured by a resistive feedback transimpedance amplifier (R-TIA) 270. The output of the R-TIA is bandpass filtered using the impedance of the sensor and the R-TIA bandwidth to limit the noise, for example. In some embodiments, the system 260 can include a zero-crossing detector 275 to preserve only the zero crossings of the signal. In this example, an AC-coupling capacitor in conjunction with a self-biased inverter sized the same as the first inverter in the chain are connected to the output of the R-TIA 270. The inverter chain maintains the zero crossings while transforming the signal into a rail-to-rail square wave, $\varphi_{sig}$ and $\varphi_{ref}$ from the signal and reference electrode, respectively. The phase of the signal pixel $\varphi_{sig}$ is then compared with the phase cord from an identical pixel attached to a reference sensor (one for each column in the array that functions as the experimental control) via a phase detector 280, e.g., which in some embodiments can include an XOR logic gate, to produce a pulse $\varphi_{diff}$ with a duty cycle linearly proportional to the phase difference. The reference pixels enable a pseudo-differential measurement to cancel common-mode variations (to the first order) such as temperature drift, process variation, and non-specific binding, for example. An additional delay is included in the reference path to remove the dead-zone caused by mismatch and noise such that a zero-phase difference still produces a well-defined minimum XOR pulse. The system 260 includes a time-to-digital converter (TDC) 290, which, in some embodiments, includes a first-order noise-shaped gated ring oscillator (GRO) 291 converts the pulses to a digital output $D_{out}$. Since the sinusoidal stimulus waveform is continuous, the TDC 290 accumulates consecutive XOR pulses.

FIG. 2C also shows an inset diagram 265 that illustrates a cross-sectional view of an example embodiment of the layers of a sensor pixel of the biosensor chip 210. In this example, the electrode layer 266 comprises gold and is arranged on top of an intermediary metallic layer 267, which can comprise one or more metals to adhere and electrically interface the electrode layer 266 to the in-pixel circuitry layer 269 under the intermediary metallic layer 267. In this example, the intermediary metallic layer 267 includes nickel, and the in-pixel circuitry layer 269 includes contact regions with an electrically conductive material, e.g., aluminum.

In-Pixel Averaging Time-to-Digital Converter

Figure 3:
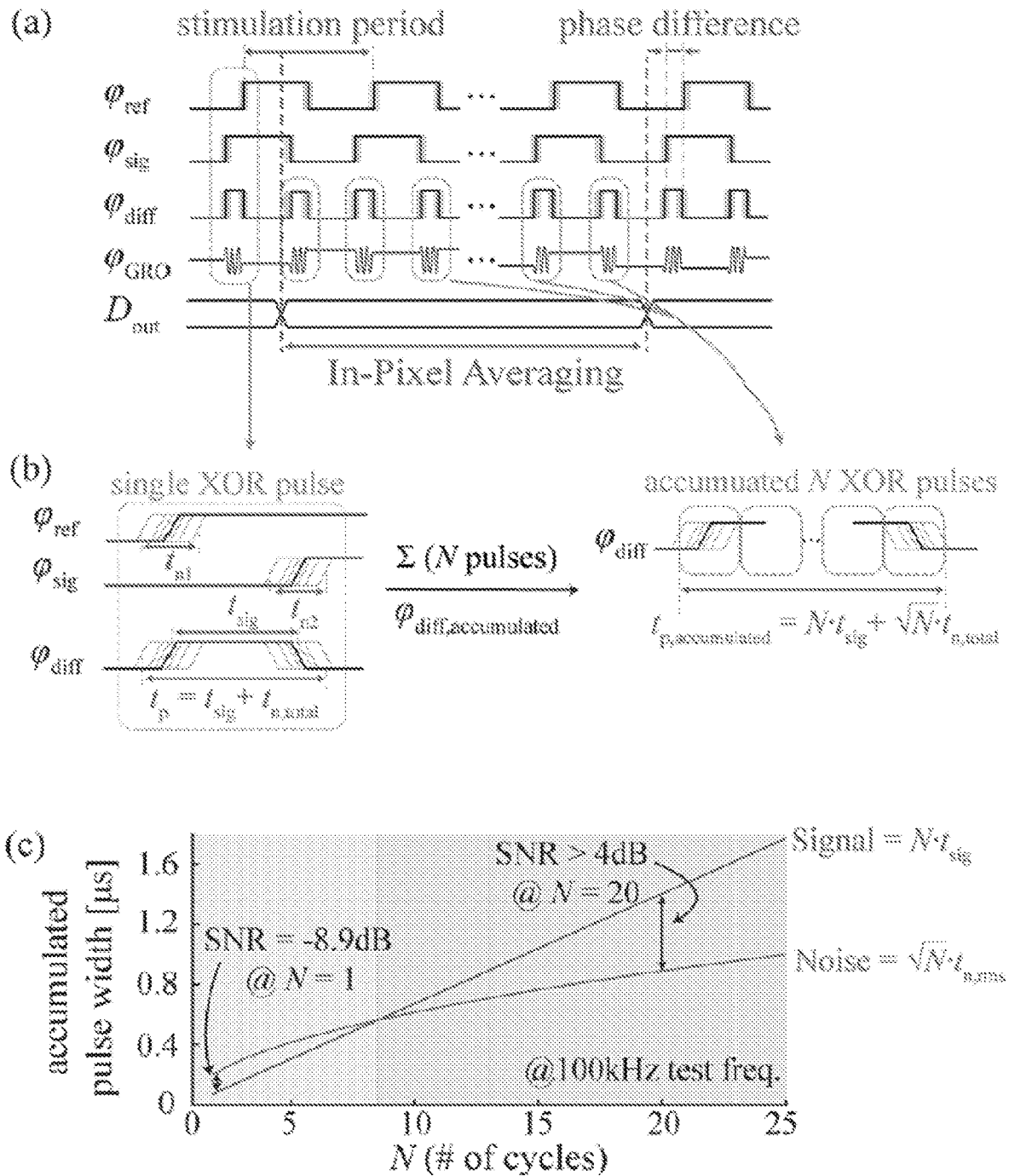
FIG. 3 shows plots of (a) example waveforms showing the concept of phase difference averaging by accumulating several XOR pulses, (b) an example single XOR pulse with jitter before and after accumulation, and (c) example simulation results showing the SNR increasing 3 dB with every 2× integration time.

In example implementations of the system 260, the TDC 290 performs the pulse width to digital conversion of $\varphi_{diff}$ by only turning on the GRO 291 when $\varphi_{diff}$ is high, as shown in panel (a) of FIG. 3. The phase changes of one stage in the GRO 291 in each stimulation period ($T_{stim}=1/f_{stim}$) is:

$$\varphi_{GRO}=2\pi f_{GRO}\times T_{stim}\times(\text{Duty Cycle of }\varphi_{diff})\text{rad} \quad (1)$$

where $f_{GRO}$ is the free running frequency of the GRO 291. Therefore, the duty cycle of $\varphi_{diff}$ can be obtained by quantizing and normalizing $\varphi_{GRO}$ to $f_{GRO}$, and the quantized phase of the GRO 291 provides inherent first-order noise-shaping since $\varphi_{GRO}$ is an integrated version of $\varphi_{diff}$ when the GRO 291 is not reset.

FIG. 3 shows plots of (a) example waveforms showing the concept of phase difference averaging by accumulating several XOR pulses, (b) an example single XOR pulse with jitter before and after accumulation, and (c) example simulation results showing the SNR increasing 3 dB with every 2× integration time.

Each XOR pulse contains the desired phase difference, $t_{sig}$, due to the sensor impedance change, but is corrupted by noise, $t_{n1,2}$, from the sensor, R-TIA, and other circuitry that is subsequently converted into jitter, for example, as shown in panel (b) of FIG. 3. To improve the SNR of the phase measurements, for example, multiple XOR pulses are accumulated in the GRO. Since the phase noise is white within the frequency range of interest, the accumulation of N XOR pulses scales the signal amplitude by N while the noise is only scaled by √N, e.g., thereby improving the SNR by 3 dB when the integration time is doubled. For example, this SNR improvement enabled the noise requirements of the TIA and TDC to be relaxed since it is no longer necessary to lower the phase noise of a single pulse down to sub-ns for <0.1% TDC error. As presented in the example simulation results shown in panel (c) of FIG. 3, including values from a jitter of 200 $ns_{rms}$, the SNR increases from −8.9 dB to 4 dB by increasing the integration time of the TDC from 10 μs (a single XOR pulse) to 200 μs (20 XOR pulses) at a stimulus frequency of 100 kHz.

Panel (c) of FIG. 3 shows that as the number of cycles (N) is increased, the SNR is increased, which is done within each sensor pixel of the biosensor chip 210. For example, if the reference signal frequency (f) is set at 1 kHz by the signal generator 250, then every 1 millisecond the system 200 can compute two zero products (a positive and a negative cycle); whereas if f is set at 10 kHz, then a cycle is computed every 0.1 millisecond, allowing for 10x more measurements to be averaged within the pixel. As the measurement time is increased, the signal-to-noise ratio is increased. By measuring more than one cycle, the system 200 is able to extract the signal out of what would nominally be in the noise (e.g., white noise in the system).

Example Implementations

An example EIS biosensor chip was used in the example implementations, which included 16×20 pixels with the first row serving as reference pixels and the remaining 19 rows as signal pixels. Each reference pixel generates a reference signal for the signal pixels in the same column. The area of a pixel is 140×140 $\mu m^2$ with an electrode area of 100×100 $\mu m^2$ using the top metal layer without any passivation. In this example, all the circuitry, including R-TIA, inverter chain, and in-pixel averaging TDC are placed beneath this electrode. The R-TIA was designed with a gain of 100 kΩ and implemented using a two-stage, folded cascode amplifier, as shown in FIG. 4B. The amplifier was designed with a flicker noise corner frequency of less than 1 kHz by sizing the input devices and using source degeneration on the load devices. The second stage of the amplifier provides the necessary low output impedance to drive the feedback resistor. In simulation, the amplifier in open-loop achieves 100 dB DC gain and 36 MHz unity-gain bandwidth while consuming 142 μW.

FIG. 4A shows a schematic of an example R-TIA with an AC-coupling capacitor.

FIG. 4B shows an example folded cascode amplifier with source degeneration to reduce flicker noise.

The application and the polar phase detection scheme are tolerant of mismatch (e.g., the offset of the amplifier, the delay of inverter chain, etc.) because any mismatch is converted into a constant phase shift at the output of the R-TIA and a constant duty cycle offset at the output of the XOR. However, the XOR does not provide differentiation between phase leading or lagging between the reference and signal pixels, so an explicit delay chain of 250 ns delay was added to guarantee a minimum pulse width at the XOR output even with noise and mismatch from the in-pixel circuitry (e.g., the signal pixel always sets the rising edge of the pulse whereas the reference pixel determines the falling edge). The inverter chain in the reference pixels was sized larger to minimize mismatch between the reference and the signal pixels. This reduced offset also allows the delay in the reference pixel to be shorter thereby reducing its area.

Figure 5:
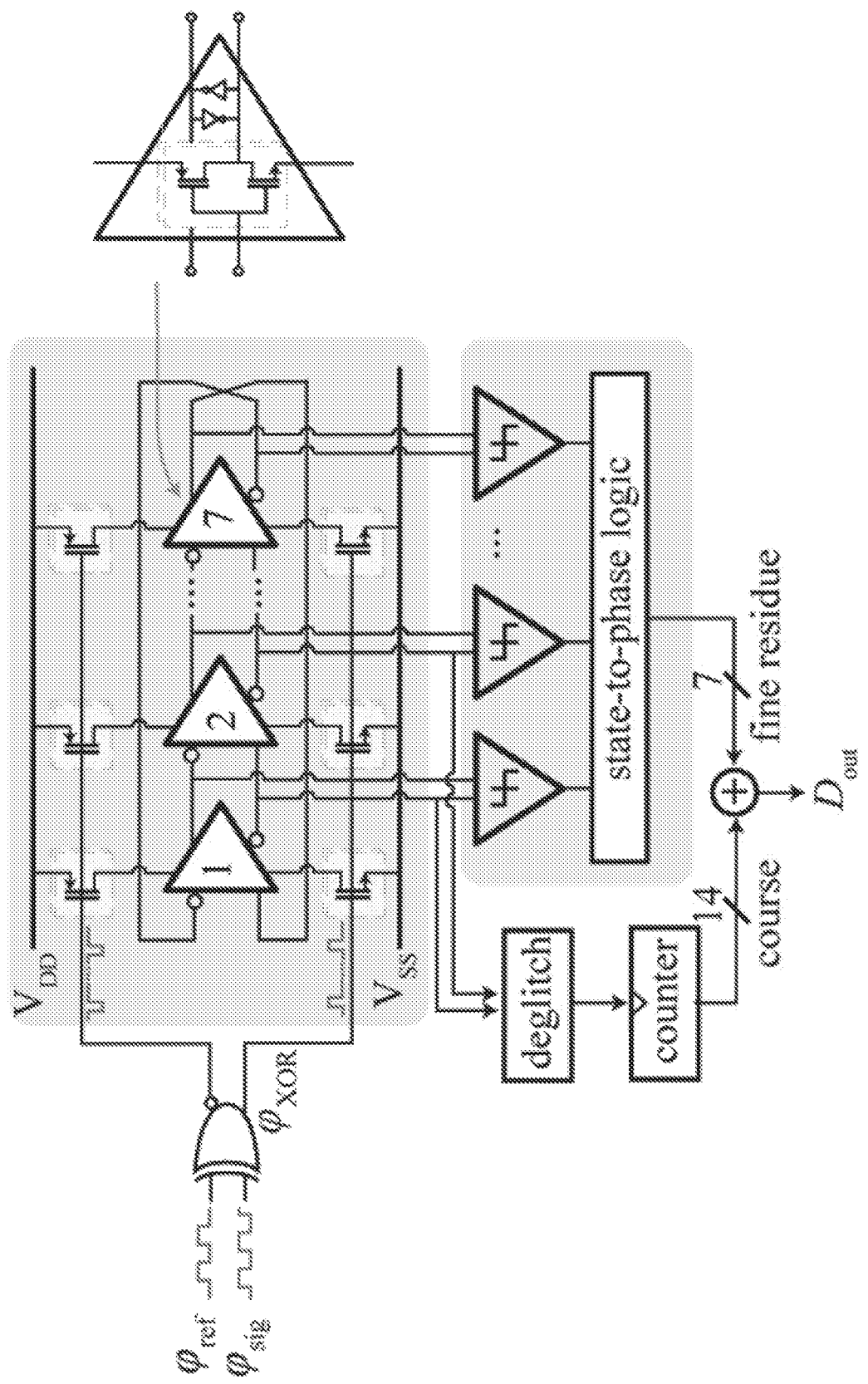
FIG. 5 shows a schematic of an example in-pixel averaging phase-to-digital converter using a 7-stage pseudo-differential gated-ring oscillator.

FIG. 5 shows a schematic of an example in-pixel averaging phase-to-digital converter using a 7-stage pseudo-differential gated-ring oscillator.

The example TDC was implemented as a 7-stage pseudo-differential GRO designed to balance the noise (white and flicker) and power trade-off, as shown in FIG. 5. When the XOR output is high, this GRO converts the duty cycle of the XOR pulse to phase with a gain of 609 krad/%. Multiple XOR pulses are accumulated in the phase domain, and the phase is stored as voltage on the capacitance at the output node of each stage when the GRO is turned off. The GRO was sized such that the leakage current introduces negligible error in the off state. For coarse phase-to-digital conversion, a counter is used to quantize the phase change $\varphi_{GRO}$ of every $2\pi$ rad of the oscillation. Measuring the state of the ring oscillator using clocked sense amplifiers adds $\pi/7$ fine quantization levels. The clock for the sense amplifier was synchronized with the readout frequency of $f_{stim}/N$ rather than $f_{stim}$ to minimize kickback noise to the GRO. The counter was designed with a 14-bit depth to be able to handle a maximum integration time of 10 ms without overflowing. The combined coarse and fine data from the counter and the comparator conversions respectively provide a 21-bit digital output for each of the pixels. The output of each pixel is readout using a serial peripheral interface (SPI) bus, and the output of 16 pixels in each row are concatenated to a 1-bit width and 336-bit length digital output format. Therefore, the clock frequency for the SPI is 336× the readout rate.

Example Measurement Results

Example Electrical Measurements

The performance of the in-pixel circuitry was characterized using a mock electrochemical cell, like that shown in FIG. 1A, e.g., made from a network of passive components for both the signal and reference channels. This example mock cell has an equivalent impedance of a gold-plated 100×100 $\mu m^2$ electrode (the same as the on-chip electrodes) in a 4×SSC (saline-sodium citrate) buffer. The linearity was measured by applying two sinusoids with a phase shift between the reference and signal pixel using an arbitrary function generator.

Figure 6A:
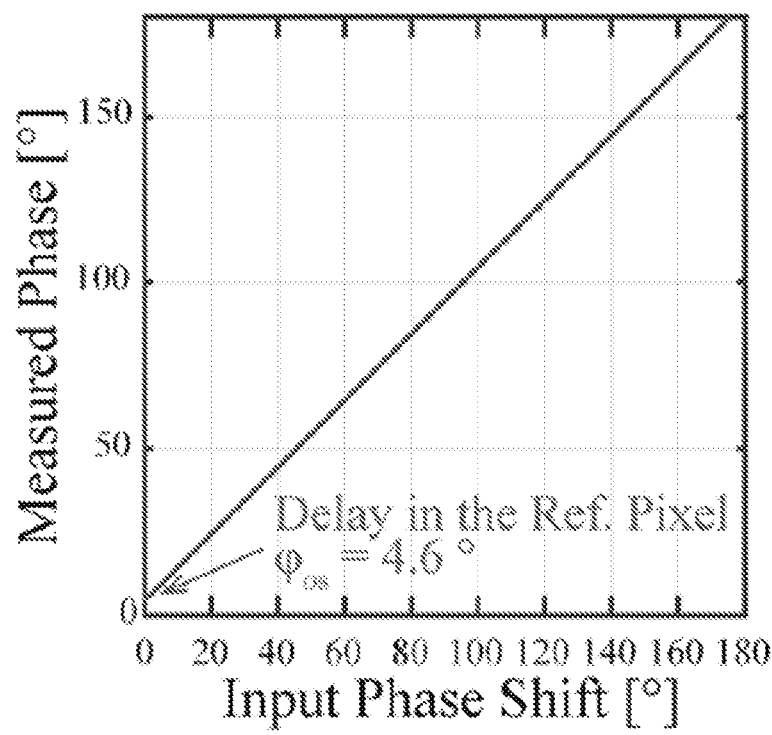
FIGS. 6A-6D show data plots of an example characterization of the in-pixel circuitry with a mock cell, depicting the transfer function and linearity, noise of single cycle, and SNR improvement with the in-pixel averaging by accumulating multiple cycles.
Figure 6B:
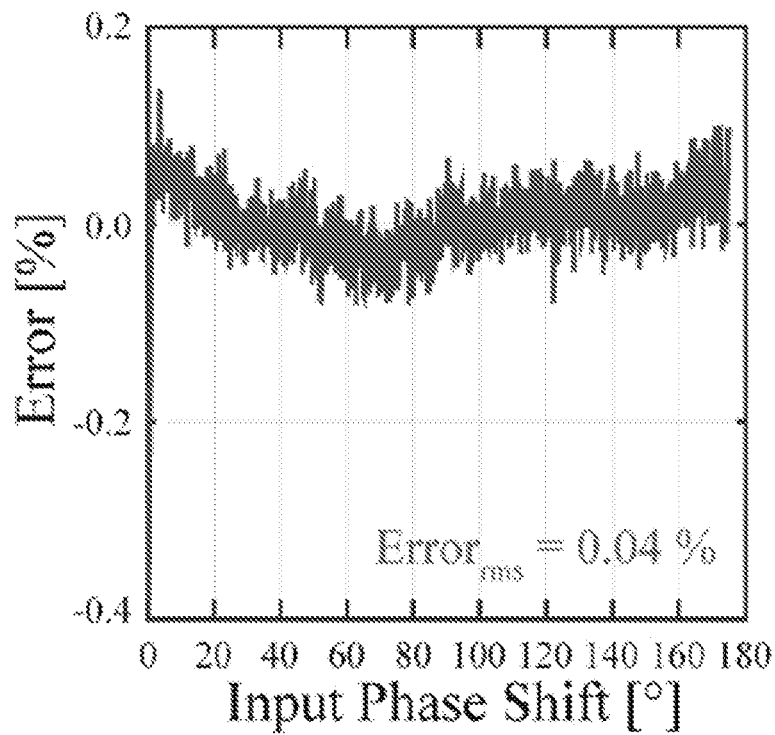
Figure 6C:
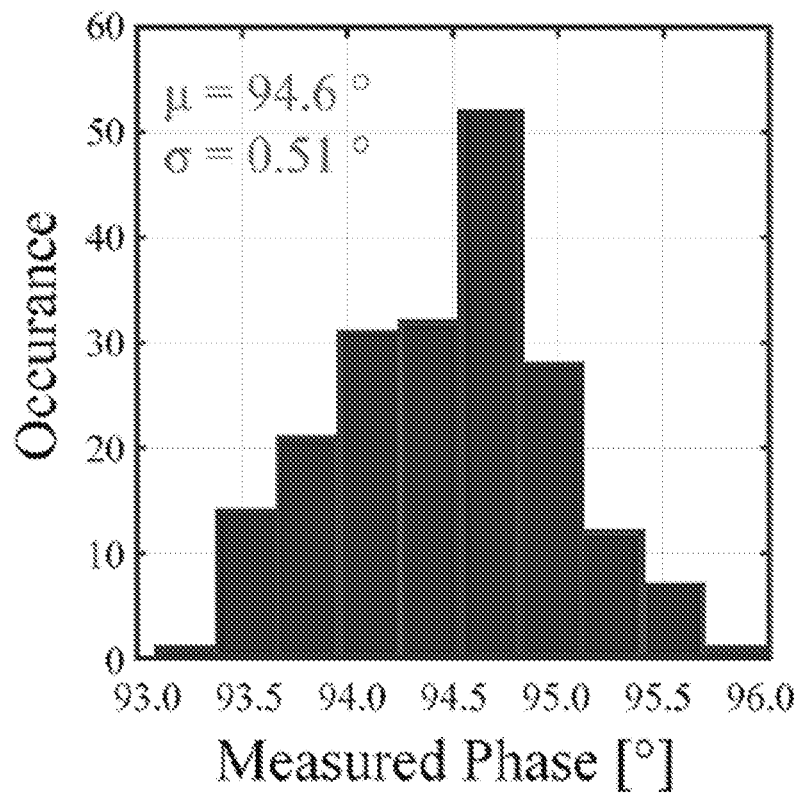
Figure 6D:
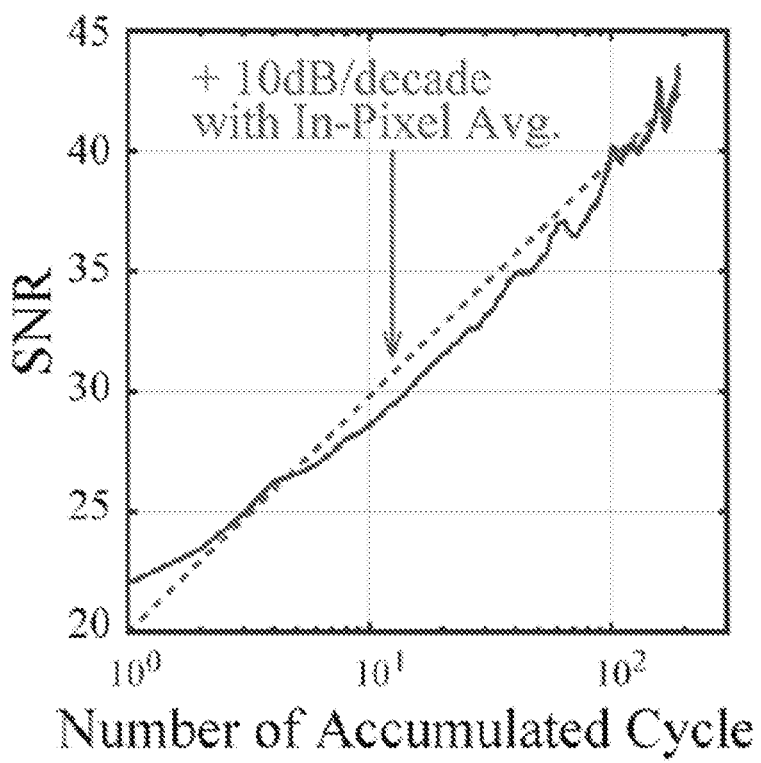

FIGS. 6A-6D show data plots of an example characterization of the in-pixel circuitry with a mock cell, depicting the transfer function (FIG. 6A) and linearity (FIG. 6B), noise of single cycle (FIG. 6C), and SNR improvement (FIG. 6D) with the in-pixel averaging by accumulating multiple cycles. The example results showed an offset of 4.6° (e.g., 250 ns) matching the designed delay chain in the reference pixel (FIG. 6A), and an RMS linearity error of 0.04% over a phase full scale range of 175.4° (FIG. 6B) at a test frequency of 50 kHz. The noise was characterized by providing a constant 90° phase shift between the reference and a signal pixel. FIG. 6C shows a histogram of a single counter output with an RMS noise of 0.51°, and measured data demonstrating that the in-pixel averaging technique provides an SNR improvement of +10 dB per 10× integration time (FIG. 6D).

Example Biological Measurements

In the example implementations, before making biological measurements, each sensor was plated with gold for electrochemical compatibility using a standard ENIG process (e.g., Stapleton Technologies, Inc.). To verify the operation of the sensor array, each bare gold electrode in the array was used to measure the phase change at varying buffer strengths that shift the solution resistance and double-layer capacitances of the electrode's impedance model. As demonstrated in FIG. 7A, where 1 μL of 20×SSC buffer was repeatedly added to an initial sample of 45 μL 3×SSC and measured by the chip, the change in impedance due to the increase in the buffer strength from 3× to 4.3× causes a direct and detectable change in phase.

Figure 7B:
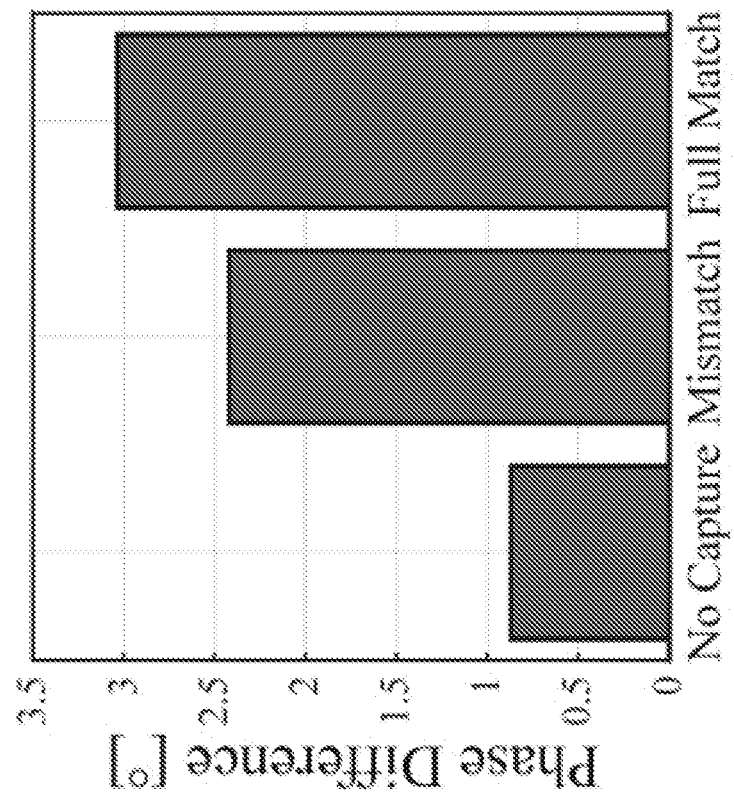
FIG. 7B shows a data plot depicting the average phase change due to hybridization, where Zika ssDNA binds to the surface.
Figure 7A:
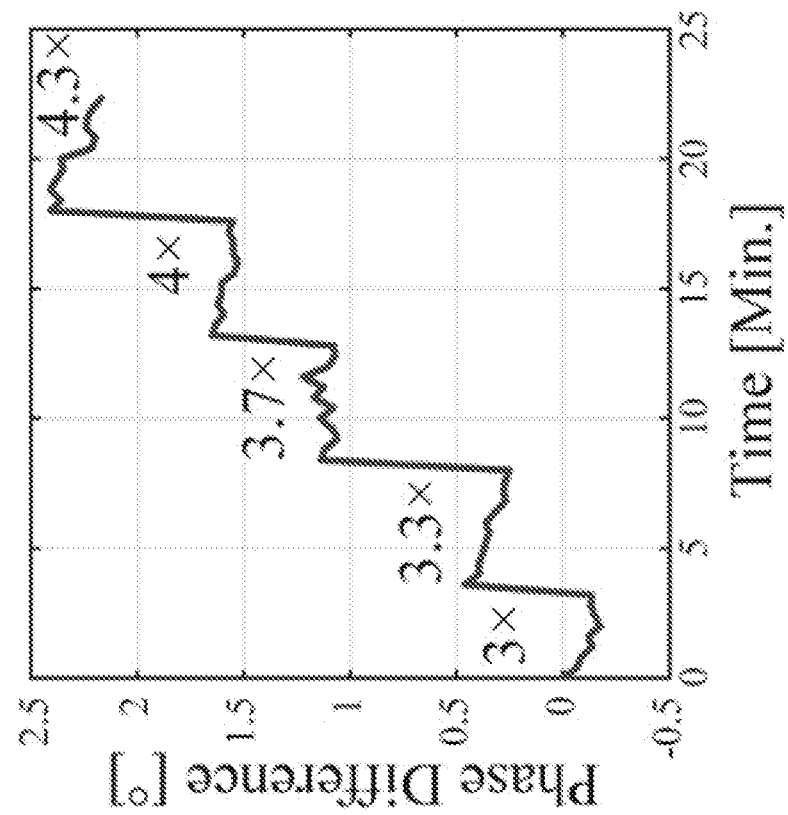
FIG. 7A shows a data plot depicting a phase change due to increasing buffer strength of a single sensor.

FIG. 7A shows a data plot depicting a phase change due to increasing buffer strength of a single sensor. FIG. 7B shows a data plot depicting the average phase change due to hybridization, where Zika ssDNA binds to the surface.

Next, a single sensor array was functionalized with two types of 30 nucleotide single-stranded DNA (ssDNA) capture probes. The first is the complimentary capture strand (5'GCTTGGCCAGGTCACTCATTGAAAATCCTC)(SEQ ID NO: 1), which is intended to fully capture a target DNA probe used to detect the Zika virus. The second is the 15-base pair mismatch capture strand (5'GCTTGGCCAGGTCACGTGCCTGGGGGCAAGA) (SEQ ID NO: 2), where only half of the oligonucleotide is complimentary to the target causing only partial binding. During the hybridization step, 50 μL of 1 μM target oligonucleotide was added and impedance measurements were made to detect the binding of the target to the probes. As shown in FIG. 7B, the example on-chip sensors can measure this hybridization in real-time and distinguish between complimentary and mismatched strands.

Figure 8:
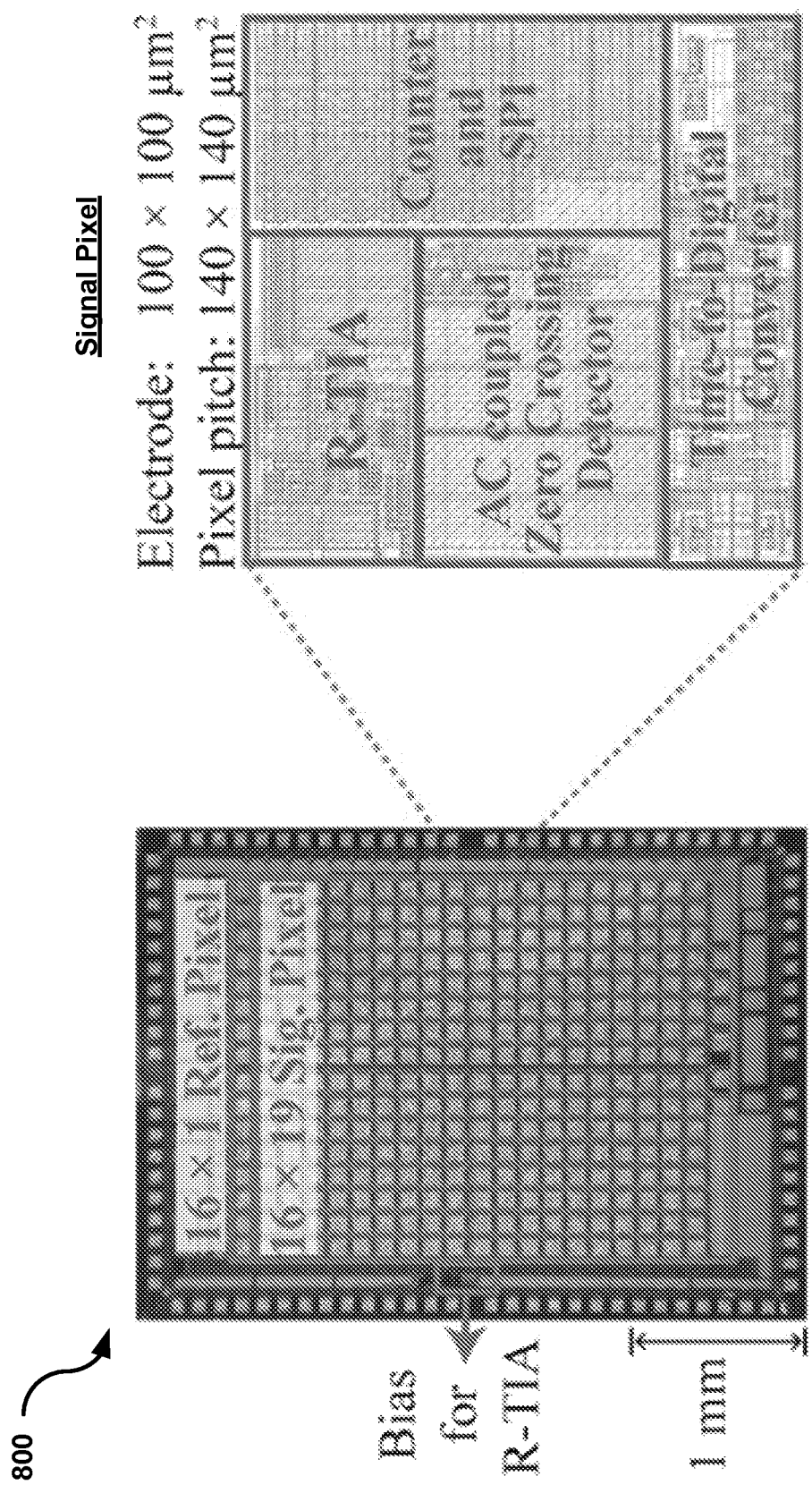
FIG. 8 shows an image of an example embodiment of an on-chip biosensor array device in accordance with the present technology.

FIG. 8 shows an image of an example embodiment of an on-chip biosensor array device 800. The image in FIG. 8 depicts an annotated die photo of the example on-chip biosensor array device 800, with an inset (on the right) depicting the design and layout of an example signal pixel of the biosensor array device 800. The example chip was fabricated in a TSMC 0.18 µm CMOS process with a 1.8 V supply voltage. The example biosensor device 800 was used in example implementations and demonstrated the capability to achieve the highest pixel density with completely in-pixel analog frontend and quantizer circuitry. As shown by the results of example implementations, the disclosed polar phase detection and in-pixel averaging technique provided 3× less phase error, e.g., as compared to the conventional 'state-of-the-art', allowing ultra-sensitive bioassays.

Table 1 summarizes some features and/or example performance of the example device 800 shown in FIG. 8 as compared with existing EIS devices. In Table 1, the existing EIS devices include the EIS device described by Yang. et al., titled "Compact Low-Power Impedance-to-Digital Converter for Sensor Array Microsystems" ("JSSC 2009"); the EIS device described by Manickam et al., titled "A CMOS Electrochemical Impedance Spectroscopy Biosensor Array for Label-Free Biomolecular Detection" ("ISSCC 2010"); the EIS device described by Mazhab-Jafari et al., titled "16-Channel CMOS Impedance Spectroscopy DNA Analyzer With Dual-Slope Multiplying ADCs" ("TBCAS 2012"); and the EIS device described by Chen et al., titled "Novel 10-Bit Impedance-to-Digital Converter for Electrochemical Impedance Spectroscopy Measurements" ("JSSC 2017").

cloud, and/or one or more mobile computing devices, such as a smartphone, tablet, or wearable computer device including a smartwatch or smartglasses. The data processing unit includes a processor to process data, and memory in communication with the processor to store and/or buffer data. For example, the processor can include a central processing unit (CPU) or a microcontroller unit (MCU). In some implementations, the processor can include a field-programmable gate-array (FPGA) or a graphics processing unit (GPU). For example, the memory can include and store processor-executable code, which when executed by the processor, configures the data processing unit to perform various operations, e.g., such as receiving information, commands, and/or data, processing information and data, such as from the biosensor device, and transmitting or providing processed information/data to another device, such as an actuator or external display. To support various functions of the data processing unit, the memory can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory. In some implementations, the data processing unit includes an input/output (I/O) unit to interface the processor and/or memory to other modules, units or devices. In some embodiments, such as for mobile computing devices, the data processing unit includes a wireless communications unit, e.g., such as a transmitter (Tx) or a transmitter/receiver (Tx/Rx) unit. For example, in such embodiments, the I/O unit can interface the processor and memory with the wireless communications unit, e.g., to utilize various types of wireless interfaces compatible with typical data communication standards, which can be used in communications of the data processing unit with other devices, e.g., such as

TABLE 1

|  | JSSC 2009 | ISSCC 2010 | TBCAS 2012 | TBCAS 2017 | This Work |
|---|---|---|---|---|---|
| Tech. [µm] | 0.5 | 0.35 | 0.13 | 0.35 | 0.18 |
| Supply [V] | 3 | 3.3 | 1.2 | 3.3 | 1.8 |
| On-Chip Electrodes? | No | Yes | Yes | No | Yes |
| Num. Sensors | — | 100 | 64 | — | 320 |
| Num. Readout Channels | 1 | 100 | 16 | 1 | 320 |
| Area/Ch. [µm$^2$] | 60,000 | 10,000* | 60,000 | 70,000 | 19,600 |
| Power [mW] | 0.006 | 84.5 | 0.35 | 0.32 | 63 |
| Power/Ch. [µW] | 6 | 845 | 5.57 | 320 | 197 |
| ADC | On Chip | Off Chip | In Pixel | In Pixel | In Pixel |
| Freq. Range [Hz] | $0.1$-$10^4$ | $10^2$-$5 \times 10^7$ | $0.1$-$10^4$ | $10^{-4}$-$10^5$ | $5 \times 10^3$-$10^6$ |
| Quadrature Signal Source Required | Yes | Yes | Yes | No | No |
| Magnitude Error | 0.32% @ 10 Hz | — | — | 0.28% @ 10 kHz | N/A |
| Phase Error | 2.7% @ 1 kHz, 38 S/s | — | — | 0.12% @ 10 Hz, 10 S/s | 0.04% @ 50 kHz, 24 S/s |

*Require additional off-chip demodulation and quantization circuit.

Figure 9:
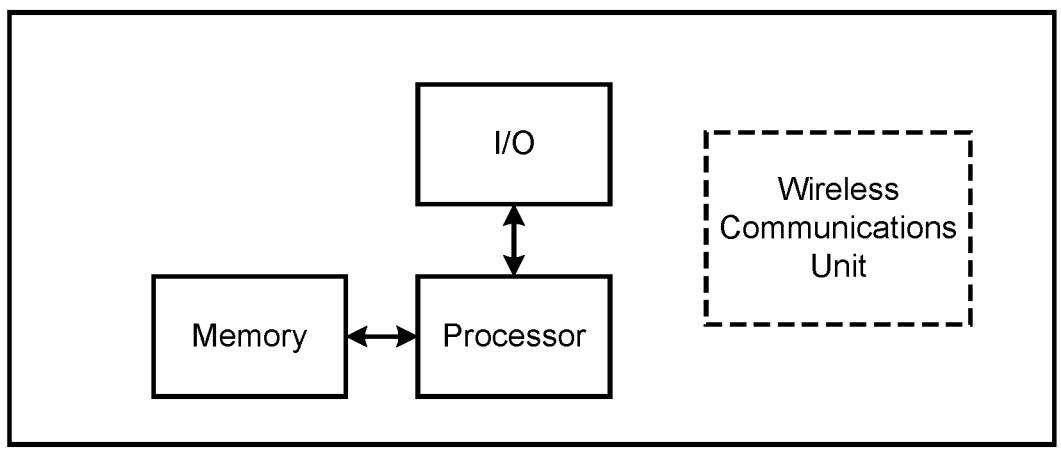
FIG. 9 shows a block diagram of an example embodiment of a data processing unit that can be configured in communication with the example on-chip biosensor array device in a biosensing system.

FIG. 9 shows a block diagram of an example embodiment of a data processing unit that can be configured in communication with the example on-chip biosensor array device in a biosensing system. In various implementations, the data processing unit is embodied on one or more personal computing devices, e.g., including a desktop or laptop computer, one or more computing devices in a computer system or communication network accessible via the Internet (referred to as "the cloud") including servers and/or databases in the cloud, and/or one or more mobile computing devices, such as between the one or more computers in the cloud and the user device. The data communication standards include, but are not limited to, Bluetooth, Bluetooth low energy (BLE), Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces. In some implementations, the data processing unit can interface with other devices using a wired connection via the I/O unit. The data processing unit can also interface with other external interfaces, sources of data storage, and/or visual or audio display devices, etc. to retrieve and transfer data and information that can be processed by the processor, stored in the memory, or exhibited on an output unit of a display device or an external device.

Herein, example embodiments and implementations are described that demonstrate a field deployable multi-pixel electrochemical CMOS biosensor array for highly scalable label-free molecular testing, including nucleic acid testing, amino acid or protein testing, or other bioassays. The on-chip sensors use a streamlined and highly scalable polar phase detection method to monitor bioassay events. In some examples, the in-pixel circuitry (e.g., 140×140 measures the necessary phase changes of the on-chip sensors using a transimpedance amplifier, zero-crossing detector, and a first-order noise-shaping time-to-digital converter without the need for quadrature signal analysis. This example mostly-digital design has the advantage of +10 dB noise reduction for each 10× additional data points by using in-pixel averaging and achieves a 0.04% RMS linearity error. For example, implemented in a 0.18 μm process, the 3×4 mm² chip achieves high sensitivity performance with an rms phase error of 0.04% at 50 kHz and was used to measure hybridization of Zika virus oligonucleotides. Using an alternative impedance measurement technique, label-free detection of DNA hybridization was measured with the designed array demonstrating promise for precise and highly scalable biosensing in POC applications.

EXAMPLES

The following examples are illustrative of several embodiments in accordance with the present technology. Other exemplary embodiments of the present technology may be presented prior to the following listed examples, or after the following listed examples.

In some embodiments in accordance with the present technology (example A1), a biosensor device includes a substrate; a circuitry layer on the substrate, comprising a resistive feedback transimpedance amplifier (R-TIA), a zero-crossing detector unit, and a first-order noise-shaping time-to-digital converter (TDC); and a sensing layer in electrical communication with the circuitry layer, comprising an array of sensor pixels including one or more reference sensor pixels and one or more signal sensor pixels arranged on the substrate, wherein the one or more signal sensor pixels include an electrode and a functionalization layer on the electrode including one or more nucleic acid strands to provide a capture probe for a target analyte for detection, and the one or more reference sensor pixels include an unfunctionalized electrode spaced from a corresponding signal sensor pixel, wherein the biosensor device is operable to detect the target analyte based on electrical signal changes caused by hybridization of the capture probe by the target analyte.

Example A2 includes the device of example A1, wherein the biosensor device is operable to detect the target analyte in a sample electrolytic solution in contact with the sensing layer by (i) applying an excitation voltage at the electrode of a corresponding signal sensor pixel at a stimulation frequency, (ii) measuring a corresponding induced current at the resistive feedback transimpedance amplifier, (iii) converting a rail-to-rail signal by the zero-crossing detector, (iv) determining a relative phase shift caused by a change of electrode impedance, and (v) quantizing and averaging a phase shift using the TDC.

Example A3 includes the device of example A2, wherein the stimulation frequency is in a range between 5 kHz and 1 MHz.

Example A4 includes the device of example A1, wherein the biosensor device is operable to monitor bioassay events based on a polar-mode measurement technique to detect the target analyte.

Example A5 includes the device of example A1, wherein the biosensor device is operable to detect the target analyte via an in-pixel digitization and accumulation of the detected signal with increased signal-to-noise ratio (SNR) of at least 10 dB for each 10× increase in readout time.

Example A6 includes the device of example A1, wherein the resistive feedback transimpedance amplifier is coupled to a bandpass filter operable to filter an output of the R-TIA using impedance of a signal sensor pixel and bandwidth of a signal from the R-TIA to limit noise of the biosensor device.

Example A7 includes the device of example A1, wherein the first-order noise-shaping time-to-digital converter (TDC) includes a first-order noise-shaped gated ring oscillator (GRO) configured to convert pulses to a digital output.

Example A8 includes the device of example A1, wherein the one or more signal sensing pixels include a plurality of the signal sensing pixels that include a variety of complimentary nucleic acid strands configured to detect a plurality of target analytes on a single biosensor device.

In some embodiments in accordance with the present technology (example A9), a point-of-care-deployable biosensor device includes a substrate; a circuitry layer on the substrate, comprising a resistive feedback transimpedance amplifier (R-TIA), a zero-crossing detector unit, and a first-order noise-shaping time-to-digital converter (TDC); and a sensing layer in electrical communication with the circuitry layer, comprising an array of sensor pixels including a row of reference sensor pixels and one or more rows of signal sensor pixels arranged on the substrate, wherein the one or more signal sensor pixels include an electrode and a functionalization layer on the electrode including one or more substances to provide a capture probe for a target analyte in an electrolytic solution, and the reference sensor pixels include an unfunctionalized electrode, wherein the biosensor device is operable to detect the target analyte based on electrical signal changes caused by hybridization of the capture probe by the target analyte.

In some embodiments in accordance with the present technology (example B1), a polar mode impedance biosensor system includes a biosensor chip device to measure impedance at an electrode-electrolyte interface, the biosensor chip comprising: (i) an array of electrodes including a working electrode and a reference electrode, wherein each respective electrode of the array corresponds to an electrochemical sensor pixel to detect an impedance change in a detected electrical signal at an outer surface of the respective electrode, and wherein the working electrode includes a functionalization layer on the outer surface of the electrode that includes one or more molecules exposing a molecular binding site to bind a target molecule for detection, and the reference electrode does not include the one or more molecules attached to the outer surface, an array of electronic circuit units corresponding to each electrochemical sensor pixel and configured in a circuitry layer of the biosensor chip device under the array of electrodes, wherein each electronic circuit includes a transimpedance amplifier electrically coupled to the electrodes of the array to amplify the detected electrical signal, a phase detector in communication with the transimpedance amplifier to determine a relative phase shift in the detected electrical signal caused by the impedance change caused by a binding event of the target molecule with the molecular binding site of the one or more molecules, and a time-to-digital converter to quantize and average phase data points in time to remove uncorrelated noise from the detected electrical signal; and a signal generator to produce an electrical excitation signal applied (i) across the electrode-electrolyte interface to be measured by the transimpedance amplifier and (ii) at the phase detector in parallel in parallel.

Example B2 includes the system of any of examples B1 or B3-B11, wherein the system is configured to detect only the phase of the impedance change.

Example B3 includes the system of any of examples B1-B2 or B4-B11, wherein the time-to-digital converter is configured to quantize and average the phase data points based on a number of cycles in a readout time that correspond to a stimulation frequency of the applied electrical excitation signal.

Example B4 includes the system of any of examples B3 or B5, wherein the stimulation frequency is in a range between 1 mHz and 10 MHz.

Example B5 includes the system of any of examples B3 or B4, wherein the system is operable to detect the target molecule based on the detected impedance change having an increased signal-to-noise ratio (SNR) of at least 10 dB for each 10× increase in the readout time.

Example B6 includes the system of any of examples B1-B5 or B7-B11, wherein the electrical excitation signal includes a sinusoidal signal.

Example B7 includes the system of any of examples B1-B6 or B8-B11, wherein the transimpedance amplifier includes a resistive feedback transimpedance amplifier that is coupled to a bandpass filter.

Example B8 includes the system of any of examples B1-B7 or B9-B11, wherein the time-to-digital converter includes a first-order noise-shaping time-to-digital converter that includes a first-order noise-shaped gated ring oscillator (GRO) configured to convert pulses to a digital output.

Example B9 includes the system of any of examples B1-B8 or B10-B11, wherein the phase detector includes an XOR logic gate operable to produce a pulse with a duty cycle linearly proportional to the relative phase shift.

Example B10 includes the system of any of examples B1-B9 or B11, wherein each electronic circuit further includes a zero-crossing detector unit electrically coupled to the output of the transimpedance amplifier and the input of the phase detector, the zero-crossing detector operable to preserve only the zero crossings of the amplified detected electrical signal.

Example B11 includes the system of any of examples B1-B10, wherein the electrochemical sensor pixel includes an electrically insulating substrate coupled to a base of the circuitry layer.

In some embodiments in accordance with the present technology (example C1), a polar mode impedance biosensor system includes a biosensor chip device to measure impedance at an electrode-electrolyte interface, the biosensor chip including: an electrochemical sensor comprising a first electrode and a second electrode to detect an impedance change in a detected electrical signal at an outer surface of the electrode, and wherein the first electrode includes a functionalization layer on the outer surface of the electrode that includes one or more molecules exposing a molecular binding site to bind a target molecule for detection, and the second electrode does not include the one or more molecules attached to the outer surface, and an electronic circuit unit corresponding to each electrode of the electrochemical sensor, wherein each electronic circuit includes a transimpedance amplifier electrically coupled to the corresponding electrode to amplify the detected electrical signal, a phase detector in communication with the transimpedance amplifier to determine a relative phase shift in the detected electrical signal caused by the impedance change caused by a binding event of the target molecule with the molecular binding site of the one or more molecules, and a time-to-digital converter to quantize and average phase data points in time to remove uncorrelated noise from the detected electrical signal; and a signal generator to produce an electrical excitation signal applied (i) across the electrode-electrolyte interface to be measured by the transimpedance amplifier and (ii) at the phase detector in parallel in parallel.

Example C2 includes the system of any of examples C1 or C3-C17, wherein the system is configured to detect only the phase of the impedance change.

Example C3 includes the system of any of examples C1-C2 or C4-C17, wherein the time-to-digital converter is configured to quantize and average the phase data points based on a number of cycles in a readout time that correspond to a stimulation frequency of the applied electrical excitation signal.

Example C4 includes the system of example C3 or C5, wherein the stimulation frequency is in a range between 1 mHz and 10 MHz.

Example C5 includes the system of example C3 or C4, wherein the system is operable to detect the target molecule based on the detected impedance change having an increased signal-to-noise ratio (SNR) of at least 10 dB for each 10× increase in the readout time.

Example C6 includes the system of any of examples C1-05 or C7-C17, wherein the transimpedance amplifier includes a resistive feedback transimpedance amplifier that is coupled to a bandpass filter.

Example C7 includes the system of any of examples C1-C6 or C8-C17, wherein the time-to-digital converter includes a first-order noise-shaped gated ring oscillator configured to convert pulses to a digital output.

Example C8 includes the system of any of examples C1-C7 or C9-C17, wherein the phase detector includes an XOR logic gate operable to produce a pulse with a duty cycle linearly proportional to the relative phase shift.

Example C9 includes the system of any of examples C1-C8 or C10-C17, wherein each electronic circuit further includes a zero-crossing detector unit electrically coupled to the output of the transimpedance amplifier and the input of the phase detector, the zero-crossing detector operable to preserve only the zero crossings of the amplified detected electrical signal.

Example C10 includes the system of any of examples C1-C9 or C11-C17, wherein the electrochemical sensor includes an array of electrodes including one or more of the first electrode and one or more of the second electrode, wherein each respective electrode of the array corresponds to an electrochemical sensor pixel to detect an impedance change in a detected electrical signal at an outer surface of the respective electrode.

Example C11 includes the system of example C10, wherein the electronic circuit units corresponding to each electrode of the electrochemical sensor is configured in an array of electronic units corresponding to the electrochemical sensor pixels.

Example C12 includes the system of example C11, wherein the array of electronic units is configured in a circuitry layer of the biosensor chip device under the array of electrodes.

Example C13 includes the system of example C12, wherein the biosensor chip device includes an electrically insulating substrate coupled to a base of the circuitry layer.

Example C14 includes the system of any of examples C1-C13 or C15-C17, wherein the electrical excitation signal includes a sinusoidal signal applied across the electrode-electrolyte interface between the electrodes of the electrochemical sensor and an external electrode.

Example C15 includes the system of example C14, wherein the first and second electrodes are operable as working electrodes, and the external electrode is operable as a counter electrode.

Example C16 includes the system of any of examples C1-C15 or C17, wherein the electrical excitation signal includes a sinusoidal signal applied across the electrode-electrolyte interface between the first electrode and the second electrode.

Example C17 includes the system of any of examples C1-C16, wherein the one or more molecules include one or more of a nucleic acid having a single-stranded region, an antibody, an antigen, an amino acid, a protein, or an aptamer.

In some embodiments in accordance with the present technology (example C18), a biosensor device includes a substrate comprising an electrically insulative material; a circuitry layer on the substrate, comprising a transimpedance amplifier, a phase detector, and a time-to-digital converter; and a sensing layer in electrical communication with the circuitry layer, comprising an array of sensor pixels including one or more reference sensor pixels and one or more signal sensor pixels arranged on the substrate, wherein the one or more signal sensor pixels include an electrode and a functionalization layer on the electrode including one or more molecules to provide a capture probe for a target analyte for detection, and the one or more reference sensor pixels include an unfunctionalized electrode spaced from a corresponding signal sensor pixel, wherein the biosensor device is operable to detect the target analyte based on electrical signal changes caused by hybridization of the capture probe by the target analyte.

Example C19 includes the device of any of examples C18 or C20-C27, wherein the biosensor device is operable to detect the target analyte in a sample electrolytic solution in contact with the sensing layer by (i) applying an excitation signal at the electrode of a corresponding signal sensor pixel at a stimulation frequency, (ii) measuring a corresponding induced current at the transimpedance amplifier, (iii) determining a relative phase shift caused by a change of electrode impedance, and (iv) quantizing and averaging a phase shift using the time-to-digital converter.

Example C20 includes the device of examples C19 or C21, wherein the stimulation frequency is in a range between 1 mHz and 10 MHz.

Example C21 includes the device of examples C19 or C20, wherein the excitation signal includes a sinusoidal signal.

Example C22 includes the device of any of examples C18-C21 or C23-C27, wherein the biosensor device is operable to detect the target analyte via an in-pixel digitization and accumulation of the detected signal with increased signal-to-noise ratio (SNR) of at least 10 dB for each 10× increase in readout time.

Example C23 includes the device of any of examples C18-C22 or C24-C27, wherein the transimpedance amplifier includes a resistive feedback transimpedance amplifier (R-TIA) that is coupled to a bandpass filter.

Example C24 includes the device of example C23, wherein the bandpass filter operable to filter an output of the R-TIA using impedance of a signal sensor pixel and bandwidth of a signal from the R-TIA to limit noise of the biosensor device.

Example C25 includes the device of any of examples C18-C24 or C26-C27, wherein the time-to-digital converter includes a first-order noise-shaped gated ring oscillator configured to convert pulses to a digital output.

Example C26 includes the device of any of examples C18-C25 or C27, wherein the one or more signal sensing pixels include a plurality of the signal sensing pixels that include a variety of complimentary single stranded nucleic acids configured to detect a plurality of target analytes on a single biosensor device.

Example C27 includes the device of any of examples C18-C26, wherein the one or more molecules include one or more of a nucleic acid having a single-stranded region, an antibody, an antigen, an amino acid, a protein, or an aptamer.

In some embodiments in accordance with the present technology (example C28), a method for polar mode impedance biosensing includes applying an electrical excitation signal at a stimulation frequency across an electrode-electrolyte interface of an electrochemical sensor of a biosensor device; measuring an electrical signal at the electrochemical sensor using a transimpedance amplifier in communication with the biosensor device; determining a relative phase shift caused by a change of electrode impedance associated with caused by a molecular binding event of a target molecule with a molecular binding site of a functionalization layer of an electrode of the electrochemical sensor, and quantizing and averaging phase data points in time to remove uncorrelated noise from the detected electrical signal.

Example C29 includes the method of any of examples C28 or C30-34, wherein the measured electrical signal includes a corresponding induced current with respect to the applied electrical excitation signal.

Example C30 includes the method of any of examples C28-29 or C31-34, wherein the stimulation frequency is in a range between 1 mHz and 10 MHz.

Example C31 includes the method of any of examples C28-30 or C32-34, wherein the excitation signal includes a sinusoidal signal.

Example C32 includes the method of any of examples C28-31 or C33-34, further comprising converting a rail-to-rail signal by a zero-crossing detector of the electronic circuit unit.

Example C33 includes the method of any of examples C28-32, wherein the method is implemented by the system of any of examples C1-C17.

Example C34 includes the method of any of examples C28-C32, wherein the method is implemented by the device of any of examples C18-C27.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A polar mode impedance biosensor system, comprising:
a biosensor chip device operable to measure impedance at an electrode-electrolyte interface between an electrode of the biosensor chip device and an electrolyte upon the electrode, the biosensor chip device comprising:
an electrochemical sensor comprising a first working electrode and a second working electrode and a background electrode to detect an impedance change in a first detected electrical signal at the first working electrode and in a second detected electrical signal at the second working electrode, respectively, and wherein the first working electrode includes a first functionalization layer on an outer surface of the first working electrode that includes one or more molecules exposing a first molecular binding site to bind a first target molecule for detection, the second working electrode includes a second functionalization layer on an outer surface of the second working electrode that includes one or more molecules exposing a second molecular binding site to bind a second target molecule for detection, and the background electrode does not include the one or more molecules of the first or second working electrode attached to an outer surface of the background electrode, and
an electronic circuit unit corresponding to each electrode of the electrochemical sensor, wherein the electronic circuit unit comprises a first electronic circuit electrically coupled to the first working electrode and a second electronic circuit electrically coupled to the second working electrode, wherein each of the first electronic circuit and the second electronic circuit of the electronic circuit unit includes: (i) a transimpedance amplifier electrically coupled to the corresponding electrode to amplify the respective detected electrical signal at the first and second working electrodes, (ii) a phase detector in communication with the respective transimpedance amplifier to determine a relative phase shift in the respective detected electrical signal caused by the impedance change caused by a binding event of the respective first or second target molecule with the respective first or second molecular binding site of the respective one or more molecules, and (iii) a time-to-digital converter to quantize and average phase data points in time to remove uncorrelated noise from the respective detected electrical signal, and wherein the electronic circuit unit further comprises a third electronic circuit electrically coupled to the background electrode that includes a third transimpedance amplifier electrically coupled to the background electrode and electrically coupled to the respective phase detector of each of the first electronic circuit and the second electronic circuit, respectively; and
a signal generator to produce an electrical excitation signal applied (i) across the electrode-electrolyte interface at the first electrode and the background electrode and across the electrode-electrolyte interface at the second electrode and the background electrode, and (ii) directly at the respective phase detector of each of the first electronic circuit and the second electronic circuit, respectively, in parallel.

2. The system of claim 1, wherein the system is configured to detect only the phase of the impedance change of at least one of the first and second working electrodes.

3. The system of claim 1, wherein the time-to-digital converter of at least one of the first electronic circuit and the second electronic circuit is configured to quantize and average the corresponding phase data points based on a number of cycles in a readout time that correspond to a stimulation frequency of the applied electrical excitation signal.

4. The system of claim 3, wherein the stimulation frequency is in a range between 1 MHz and 10 MHz.

5. The system of claim 3, wherein the system is operable to detect the first target molecule and the second target molecule based on the respective detected impedance change having an increased signal-to-noise ratio (SNR) of at least 10 dB for each 10× increase in the readout time, wherein the first target molecule and the second target molecule are a different type of molecule or a same type of molecule.

6. The system of claim 1, wherein the transimpedance amplifier of at least one of the first electronic circuit and the second electronic circuit includes a resistive feedback transimpedance amplifier that is coupled to a bandpass filter.

7. The system of claim 1, wherein the time-to-digital converter of at least one of the first electronic circuit and the second electronic circuit includes a first-order noise-shaped gated ring oscillator configured to convert pulses to a digital output.

8. The system of claim 1, wherein the phase detector of at least one of the first electronic circuit and the second electronic circuit includes an XOR logic gate operable to produce a pulse with a duty cycle linearly proportional to the corresponding relative phase shift.

9. The system of claim 1, wherein each of the first, second, and third electronic circuits further includes a zero-crossing detector unit electrically coupled to an output of the respective transimpedance amplifier and an input of the respective phase detector, the zero-crossing detector unit operable to preserve only zero crossings of an amplified detected electrical signal.

10. The system of claim 1, wherein the electrochemical sensor includes an array of working electrodes, wherein each respective working electrode of the array of working electrodes corresponds to an electrochemical sensor pixel to detect an impedance change in a detected electrical signal at an outer surface of the respective working electrode.

11. The system of claim 10, wherein the biosensor chip device includes an electrically insulating substrate coupled to a base of a circuitry layer under the array of working electrodes.

12. The system of claim 1, wherein the electrical excitation signal includes a sinusoidal signal applied across the electrode-electrolyte interface between at least one of the first working electrode or the second working electrode of the electrochemical sensor and an external electrode operable as a counter electrode.

13. The system of claim 1, wherein the electrical excitation signal includes a sinusoidal signal applied across the electrode-electrolyte interface for the first working electrode and the second working electrode.

14. The system of claim 1, wherein the one or more molecules of the first or the second working electrodes include one or more of a nucleic acid having a single-stranded region, an antibody, an antigen, an amino acid, a protein, or an aptamer.

15. A method for polar mode impedance biosensing, comprising:
applying an electrical excitation signal at a stimulation frequency across an electrode-electrolyte interface of an electrochemical sensor of a biosensor chip device, wherein the electrochemical sensor of the biosensor chip device includes a working electrode and a background electrode to detect an impedance change in a detected electrical signal at the working electrode with respect to the background electrode, wherein the working electrode includes a functionalization layer on an outer surface of the working electrode that includes one or more molecules exposing a molecular binding site to bind a target molecule for detection, and the background electrode does not include the one or more molecules attached to an outer surface of the background electrode, and wherein the biosensor chip device includes an electronic circuit unit corresponding to each electrode of the electrochemical sensor, wherein the electronic circuit unit comprises a first electronic circuit electrically coupled to the working electrode and a second electronic circuit electrically coupled to the background electrode, wherein the first electronic circuit includes: (i) a first transimpedance amplifier electrically coupled to the working electrode to amplify the detected electrical signal, (ii) a phase detector in communication with the first transimpedance amplifier, and (iii) a time-to-digital converter electrically coupled to the phase detector, and wherein the second electronic circuit includes a second transimpedance amplifier electrically coupled to the background electrode and electrically coupled to the phase detector of the first electronic circuit;
producing an electrical excitation signal, at a signal generator electrically coupled to the working and background electrodes of the electrochemical sensor and to the phase detector of the electronic circuit unit, to apply (i) across the electrode-electrolyte interface at the working electrode and at the background electrode and (ii) directly at the phase detector in parallel;
determining, at the phase detector, a relative phase shift caused by a change of electrode impedance associated with a molecular binding event of the target molecule with the molecular binding site of the functionalization layer of the working electrode of the electrochemical sensor; and
quantizing and averaging phase data points in time, at the time-to-digital converter, to remove uncorrelated noise from the detected electrical signal based on a command from a data processing unit in communication with the electronic circuit unit of the biosensor chip device.

16. The method of claim 15, comprising detecting the target molecule based on the detected impedance change having an increased signal-to-noise ratio (SNR) of at least 10 dB for each 10× increase in a readout time.

17. The method of claim 15, wherein the stimulation frequency is in a range between 1 MHz and 10 MHz.

18. The method of claim 15, wherein the electrical excitation signal includes a sinusoidal signal.

19. The method of claim 15, further comprising:
converting a rail-to-rail signal by a zero-crossing detector of the electronic circuit unit.

20. A polar mode impedance biosensor system, comprising:
a biosensor chip device operable to measure impedance at an electrode-electrolyte interface between an electrode of the biosensor chip device and an electrolyte upon the electrode, the biosensor chip device comprising:
an electrochemical sensor comprising a working electrode and a background electrode to detect an impedance change in a detected electrical signal at the working electrode with respect to the background electrode, wherein the working electrode includes a functionalization layer on an outer surface of the working electrode that includes one or more molecules exposing a molecular binding site to bind a target molecule for detection, and the background electrode does not include the one or more molecules attached to an outer surface of the background electrode,
an electronic circuit unit corresponding to each electrode of the electrochemical sensor, wherein the electronic circuit unit comprises a first electronic circuit electrically coupled to the working electrode and a second electronic circuit electrically coupled to the background electrode, wherein the first electronic circuit includes: (i) a first transimpedance amplifier electrically coupled to the working electrode to amplify the detected electrical signal, (ii) a phase detector in communication with the first transimpedance amplifier to determine a relative phase shift in the detected electrical signal caused by the impedance change caused by a binding event of the target molecule with the molecular binding site of the one or more molecules, and (iii) a time-to-digital converter to quantize and average phase data points in time to remove uncorrelated noise from the detected electrical signal, and wherein the second electronic circuit includes a second transimpedance amplifier electrically coupled to the background electrode and electrically coupled to the phase detector of the first electronic circuit;

a signal generator to produce an electrical excitation signal applied (i) across the electrode-electrolyte interface at the working electrode and at the background electrode and (ii) directly at the phase detector of the first electronic circuit in parallel; and a data processing unit comprising a processor and a memory coupled to the processor, the data processing unit in communication with the electronic circuit unit of the biosensor chip device and operable to control the time-to-digital converter to quantize and average the phase data points in time to remove the uncorrelated noise from the detected electrical signal.

21. The system of claim 20, wherein the time-to-digital converter is configured to quantize and average the phase data points based on a number of cycles in a readout time that correspond to a stimulation frequency of the applied electrical excitation signal.

22. The system of claim 20, wherein the time-to-digital converter includes a first-order noise-shaped gated ring oscillator configured to convert pulses to a digital output.

23. The system of claim 20, wherein the phase detector includes an XOR logic gate operable to produce a pulse with a duty cycle linearly proportional to the relative phase shift.

24. The system of claim 20, wherein each of the first and second electronic circuits further includes a zero-crossing detector unit electrically coupled to an output of the respective transimpedance amplifier and an input of the phase detector, the zero-crossing detector unit operable to preserve only zero crossings of an amplified detected electrical signal.

* * * * *

UNITED STATES PATENT AND TRADEMARK OFFICE
CERTIFICATE OF CORRECTION

| | | |
|---|---|---|
| PATENT NO. | : 12,157,914 B2 | Page 1 of 1 |
| APPLICATION NO. | : 16/976464 | |
| DATED | : December 3, 2024 | |
| INVENTOR(S) | : Drew Hall et al. | |

It is certified that error appears in the above-identified patent and that said Letters Patent is hereby corrected as shown below:

On the Title Page
On Page 2, in Item (56), under "OTHER PUBLICATIONS", in Column 1, Line 6, delete "p." and insert --pp.--, therefor.
On Page 2, in Item (56), under "OTHER PUBLICATIONS", in Column 2, Line 1, delete "(Investigating" and insert --Investigating--, therefor.
On Page 2, in Item (56), under "OTHER PUBLICATIONS", in Column 2, Line 29, delete "Amr ," and insert --Amr,--, therefor.

In the Specification
In Column 7, Line 55, delete "ΔC-coupling" and insert --AC-coupling--, therefor.
In Column 7, Line 62, delete "cord" and insert --$\varphi$ref--, therefor.
In Column 9, Line 5, delete "lox" and insert --10×--, therefor.
In Column 13, Line 15, delete "(e.g., 140×140" and insert --(e.g., 140×140 $\mu m^2$)--, therefor.
In Column 16, Line 52, delete "C1-05" and insert --C1-C5--, therefor.

Signed and Sealed this
Eleventh Day of March, 2025

Coke Morgan Stewart
*Acting Director of the United States Patent and Trademark Office*

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Synthetic

<400> SEQUENCE: 1
gcttggccag gtcactcatt gaaaatcctc                                        30

<210> SEQ ID NO 2
<211> LENGTH: 31
<212> TYPE: DNA
<213> ORGANISM: Artificial Sequence
<220> FEATURE:
<223> OTHER INFORMATION: Synthetic

<400> SEQUENCE: 2
gcttggccag gtcacgtgcc tgggggcaag a                                      31
```